US011766246B2

United States Patent
Ebata

(10) Patent No.: US 11,766,246 B2
(45) Date of Patent: Sep. 26, 2023

(54) ACOUSTIC WAVE DIAGNOSTIC APPARATUS AND CONTROL METHOD OF ACOUSTIC WAVE DIAGNOSTIC APPARATUS

(71) Applicant: FUJIFILM Corporation, Tokyo (JP)

(72) Inventor: Tetsurou Ebata, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 686 days.

(21) Appl. No.: 16/994,814

(22) Filed: Aug. 17, 2020

(65) Prior Publication Data

US 2020/0375578 A1 Dec. 3, 2020

Related U.S. Application Data

(63) Continuation of application No. PCT/JP2019/004742, filed on Feb. 8, 2019.

(30) Foreign Application Priority Data

Mar. 1, 2018 (JP) .................. 2018-036463

(51) Int. Cl.
*A61B 5/107* (2006.01)
*A61B 8/00* (2006.01)
*A61B 5/00* (2006.01)

(52) U.S. Cl.
CPC .............. *A61B 8/54* (2013.01); *A61B 5/0095* (2013.01); *A61B 8/461* (2013.01); *A61B 8/469* (2013.01)

(58) Field of Classification Search
CPC ......... A61B 8/54; A61B 3/0095; A61B 8/461; A61B 8/469
(Continued)

(56) References Cited

U.S. PATENT DOCUMENTS 6,569,101 B2 * 5/2003 Quistgaard .............. A61B 8/56
600/459
9,939,414 B2 * 4/2018 Tateyama ................ G01N 29/30
(Continued)

FOREIGN PATENT DOCUMENTS

JP 2002-065667 A 3/2002
JP 2010-240198 A 10/2010
(Continued)

OTHER PUBLICATIONS

International Search Report issued in PCT/JP2019/004742; dated Apr. 2, 2019.
Written Opinion issued in PCT/JP2019/004742: dated Apr. 2, 2019.

*Primary Examiner* — George B Bennett
(74) *Attorney, Agent, or Firm* — Studebaker & Brackett PC

(57) ABSTRACT

An acoustic wave diagnostic apparatus 1 includes a display unit 7, an operation unit 16, a user identification information acceptance unit 15 that accepts user identification information, a measurement item designation acceptance unit 13 that accepts a measurement item, a detection and measurement algorithm setting unit 9 that sets a detection and measurement algorithm from the measurement item, a position designation acceptance unit 14 that accepts designation of a measurement position from the operation unit 16, a measurement unit 8 that performs detection and measurement of a measurement target using a scan range on the basis of the measurement position and the detection and measurement algorithm and causes the display unit 7 to display a measurement result, a scan range modification unit 10 that modifies the scan range, and a scan range memory 11 that stores the modified scan range for each piece of user identification information, and the measurement unit 8
(Continued)

detects the measurement target using the modified scan range from the next measurement.

20 Claims, 18 Drawing Sheets

(58) Field of Classification Search
USPC .......................................................... 33/512
See application file for complete search history.

(56) References Cited

U.S. PATENT DOCUMENTS

| | | | |
|---|---|---|---|
| 11,006,837 B2* | 5/2021 | Miyachi | A61B 5/0095 |
| 11,058,357 B2* | 7/2021 | Ohishi | A61B 8/4281 |
| 11,510,657 B2* | 11/2022 | Omero | A61B 8/461 |
| 2015/0005630 A1* | 1/2015 | Jung | A61B 8/468 |
| | | | 600/437 |
| 2015/0297175 A1* | 10/2015 | Kanayama | A61B 8/5207 |
| | | | 600/437 |
| 2016/0063702 A1 | 3/2016 | Yang et al. | |
| 2016/0338595 A1* | 11/2016 | Tateyama | G01N 21/1702 |
| 2017/0071579 A1* | 3/2017 | Ko | A61B 8/4483 |
| 2018/0214027 A1* | 8/2018 | Hirata | A61B 5/748 |
| 2019/0282210 A1* | 9/2019 | Nakatsuji | A61B 8/5207 |
| 2022/0265242 A1* | 8/2022 | Guraschi | A61B 8/5223 |
| 2022/0313220 A1* | 10/2022 | Takada | A61B 8/5215 |
| 2023/0190136 A1* | 6/2023 | Kumar | A61B 5/1076 |
| | | | 600/587 |

FOREIGN PATENT DOCUMENTS

| | | |
|---|---|---|
| JP | 2012-027696 A | 2/2012 |
| JP | 2013-111434 A | 6/2013 |
| JP | 2015-021915 A | 2/2015 |
| JP | 2016-043253 A | 4/2016 |
| JP | 2019-030478 A | 2/2019 |

* cited by examiner

ACOUSTIC WAVE DIAGNOSTIC APPARATUS AND CONTROL METHOD OF ACOUSTIC WAVE DIAGNOSTIC APPARATUS

CROSS-REFERENCE TO RELATED APPLICATIONS

This application is a Continuation of PCT International Application No. PCT/JP2019/004742 filed on Feb. 8, 2019, which claims priority under 35 U.S.C. § 119(a) to Japanese Patent Application No. 2018-036463 filed on Mar. 1, 2018. Each of the above applications is hereby expressly incorporated by reference, in its entirety, into the present application.

BACKGROUND OF THE INVENTION

1. Field of the Invention

The present invention relates to an acoustic wave diagnostic apparatus and a control method of the acoustic wave diagnostic apparatus, and in particular, to an acoustic wave diagnostic apparatus that performs detection and measurement of a measurement target on an acoustic wave image and a control method of the acoustic wave diagnostic apparatus.

2. Description of the Related Art

In recent years, medical acoustic wave diagnostic apparatuses generally have a measurement function of measuring the length, size, area, and the like of various organs, lesions, and the like included in an acquired acoustic wave image. In order to measure a measurement target, usually, a user operates a caliper, that is, a cursor using an input device for inputting coordinates, such as a trackpad, a trackball, and a mouse, to set a measurement point, a region of interest, or the like on a display image. As described above, in a case where a manual operation is performed by the user, there is an influence due to the user's experience, skill level, and the like, and therefore, various attempts have been made to automate the operation.

For example, JP2010-240198A discloses an ultrasound diagnostic apparatus that automatically sets optimal image mode, image quality setting, measurement mode, and measurement item for a measurement target in a case where a body mark for the measurement target is selected by a user through an operation unit. In JP2010-240198A, for an ultrasound image, a measurement target is measured based on the position, number, and order of measurement points input from the user through the operation unit, and a measurement result thereof is displayed on a display unit.

Further, JP2013-111434A discloses an ultrasound diagnostic apparatus that, in a case where a designation point is input on an ultrasound image from a user through an operation unit, determines an appropriate measurement point by performing image processing on a certain region centered on the input designation point. In JP2013-111434A, a measurement target is measured on the basis of the measurement point determined in this manner.

SUMMARY OF THE INVENTION

As described above, in the ultrasound diagnostic apparatuses disclosed in JP2010-240198A and JP2013-111434A, since it is necessary to manually designate a measurement point and a designation point through the operation unit, the measurement requires time and effort.

Thus, it is desired that when a user simply designates an approximate position on an ultrasound image in which a measurement target is present, measurement is performed by automatically searching a surrounding area of the position and detecting the measurement target.

However, the designated position of the measurement target varies greatly depending on the user, and it is assumed that there are users who accurately designate the position of the measurement target and there are also users who roughly designate the position of the measurement target. In a case where a position greatly deviated from the center of the measurement target is designated by the user, the detection of the measurement target may fail.

The invention has been made in order to solve such a problem in the related art, and an object of the invention is to provide an acoustic wave diagnostic apparatus, and a control method of the acoustic wave diagnostic apparatus which are capable of easily and accurately performing measurement regardless of the user.

In order to achieve the above object, an acoustic wave diagnostic apparatus of an aspect of the invention comprises a display unit that displays an acquired acoustic wave image; an operation unit that is used for a user to perform an input operation; a user identification information acceptance unit that accepts user identification information through the operation unit; a measurement item designation acceptance unit that accepts designation of a measurement item relating to a measurement target through the operation unit; a detection and measurement algorithm setting unit that sets a detection and measurement algorithm on the basis of the measurement item accepted by the measurement item designation acceptance unit; a position designation acceptance unit that accepts designation of a position of the measurement target on the acoustic wave image displayed on the display unit through the operation unit; a measurement unit that detects the measurement target by scanning a detection region in a scan range and measures the detected measurement target on the basis of the position of the measurement target accepted by the position designation acceptance unit and the detection and measurement algorithm set by the detection and measurement algorithm setting unit to cause the display unit to display a measurement result including a measurement point; a scan range modification unit that modifies the scan range; and a scan range memory that stores the scan range modified by the scan range modification unit in association with the user identification information, in which, from next measurement by the user, the measurement unit detects the measurement target using the scan range stored in the scan range memory.

The scan range modification unit can modify at least one of a size or a position of the scan range.

In addition, the scan range modification unit can modify the scan range on the basis of the position of the measurement target accepted by the position designation acceptance unit and the position of the measurement target detected by the measurement unit.

In this case, the measurement unit can calculate reliability of detection of the measurement target in each detection region while scanning the detection region in the scan range, and the scan range modification unit can modify the scan range on the basis of the position of the measurement target accepted by the position designation acceptance unit and a position of a center of the detection region having the maximum reliability calculated by the measurement unit.

More specifically, the scan range modification unit can calculate a deviation amount between the position of the measurement target accepted by the position designation acceptance unit and the position of the measurement target detected by the measurement unit, and modify the scan range on the basis of statistical data of the deviation amounts after the user performs a predetermined number of times of measurement.

A measurement point modification acceptance unit that accepts a modification of a position of the measurement point through the operation unit is further comprised, in which the scan range modification unit can modify the scan range on the basis of the position of the measurement target accepted by the position designation acceptance unit and the position of the measurement point accepted by the measurement point modification acceptance unit.

In this case, the scan range modification unit can calculate a temporary detection region for detecting the measurement target on the basis of the position of the measurement point accepted by the measurement point modification acceptance unit, and modify the scan range on the basis of the position of the measurement target accepted by the position designation acceptance unit and a position of a center of the temporary detection region.

Further, the scan range modification unit can cause the display unit to display that the position of the measurement point accepted by the measurement point modification acceptance unit is deviated, in a case where the position of the center of the temporary detection region is positioned outside the scan range.

In addition, the scan range modification unit can cause the display unit to display that the scan range is modified.

A reset instruction acceptance unit that accepts a reset instruction to return the scan range modified by the scan range modification unit to an initial scan range through the operation unit is further comprised, in which the measurement unit can detect the measurement target using the initial scan range in a case where the reset instruction is accepted by the reset instruction acceptance unit.

In addition, the measurement unit can cause the display unit to display the scan range in a case where the designation of the position of the measurement target is accepted by the position designation acceptance unit.

The acoustic wave image is preferably an ultrasound image or a photoacoustic image.

A control method of an acoustic wave diagnostic apparatus of another aspect of the invention comprises displaying an acquired acoustic wave image; accepting user identification information from a user; accepting designation of a measurement item relating to a measurement target from the user; setting a detection and measurement algorithm on the basis of the accepted measurement item; accepting designation of a position of the measurement target on the acoustic wave image from the user; detecting the measurement target by scanning a detection region in a scan range and measuring the detected measurement target on the basis of the accepted position of the measurement target and the set detection and measurement algorithm to display a measurement result including a measurement point; modifying the scan range; and storing the modified scan range in association with the user identification information, in which, from next measurement by the user, the measurement target is detected using the stored scan range.

According to the invention, a scan range modification unit that modifies a scan range, and a scan range memory that stores the scan range modified by the scan range modification unit in association with user identification information are comprised, a measurement unit detects a measurement target using the scan range stored in the scan range memory from the next measurement by a user, and thus it is possible to easily and accurately perform measurement regardless of the user.

DESCRIPTION OF THE PREFERRED EMBODIMENTS

Hereinafter, embodiments of the invention will be described with reference to the accompanying drawings.

Embodiment 1

Figure 1:
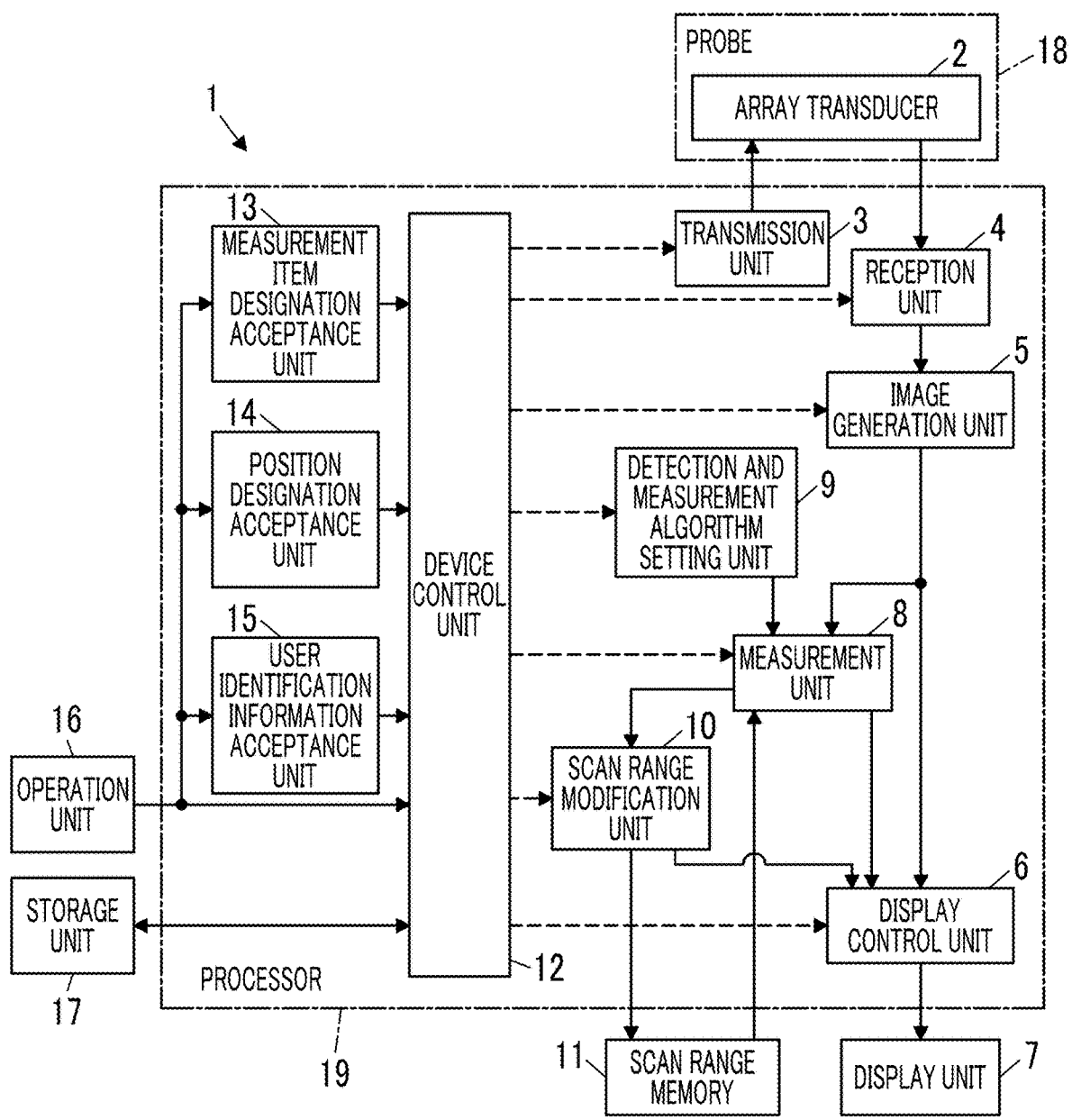
FIG. 1 is a block diagram illustrating a configuration of an ultrasound diagnostic apparatus according to Embodiment 1 of the invention.

FIG. 1 illustrates a configuration of an ultrasound diagnostic apparatus 1 according to Embodiment 1 of the invention. As illustrated in FIG. 1, the ultrasound diagnostic apparatus 1 comprises an array transducer 2, and a transmission unit 3 and a reception unit 4 are connected to the array transducer 2. Further, an image generation unit 5 is connected to the reception unit 4, and a display control unit 6 and a display unit 7 are sequentially connected to the image generation unit 5. Further, a measurement unit 8 is connected to the image generation unit 5, and the measurement unit 8 is connected to the display control unit 6. Further, a detection and measurement algorithm setting unit 9 and a scan range modification unit 10 are connected to the measurement unit 8, and a scan range memory 11 and the display control unit 6 are connected to the scan range modification unit 10. Further, the scan range memory 11 is connected to the measurement unit 8.

A device control unit 12 is connected to the transmission unit 3, the reception unit 4, the image generation unit 5, the display control unit 6, the measurement unit 8, the detection and measurement algorithm setting unit 9, and the scan range modification unit 10, and a measurement item designation acceptance unit 13, a position designation acceptance unit 14, a user identification information acceptance unit 15, an operation unit 16, and a storage unit 17 are connected to the device control unit 12. The measurement item designation acceptance unit 13, the position designation acceptance unit 14, and the user identification information acceptance unit 15 are connected to the operation unit 16. In addition, the device control unit 12 and the storage unit 17 are connected so as to exchange information bidirectionally.

The array transducer 2 is included in a probe 18. In addition, the transmission unit 3, the reception unit 4, the image generation unit 5, the display control unit 6, the measurement unit 8, the detection and measurement algorithm setting unit 9, the scan range modification unit 10, the device control unit 12, the measurement item designation acceptance unit 13, the position designation acceptance unit 14, and the user identification information acceptance unit 15 constitute a processor 19.

The array transducer 2 of the probe 18 illustrated in FIG. 1 has a plurality of ultrasonic transducers arranged in a one-dimensional or two-dimensional manner. According to a drive signal supplied from the transmission unit 3, each of the transducers transmits an ultrasonic wave and receives a reflected wave from a subject to output a reception signal. For example, each transducer is formed by using an element in which electrodes are formed at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission unit 3 of the processor 19 includes, for example, a plurality of pulse generators, and the transmission unit 3 adjusts the amount of delay of each drive signal so that ultrasonic waves transmitted from the plurality of transducers of the array transducer 2 form an ultrasound beam on the basis of a transmission delay pattern selected according to the control signal from the device control unit 12, and supplies the obtained signals to the plurality of transducers. Thus, in a case where a pulsed or continuous-wave voltage is applied to the electrodes of the transducers of the array transducer 2, the piezoelectric body expands and contracts to generate pulsed or continuous-wave ultrasonic waves from each transducer, and an ultrasound beam is formed from the combined wave of these ultrasonic waves.

The transmitted ultrasound beam is reflected by a target, for example, a site of the subject, and propagates toward the array transducer 2 of the probe 18. The ultrasonic waves propagating toward the array transducer 2 in this manner are received by each transducer constituting the array transducer 2. In this case, each transducer constituting the array transducer 2 expands and contracts by receiving the propagating ultrasound echo to generate electrical signals, and outputs the electrical signals to the reception unit 4.

Figure 2:
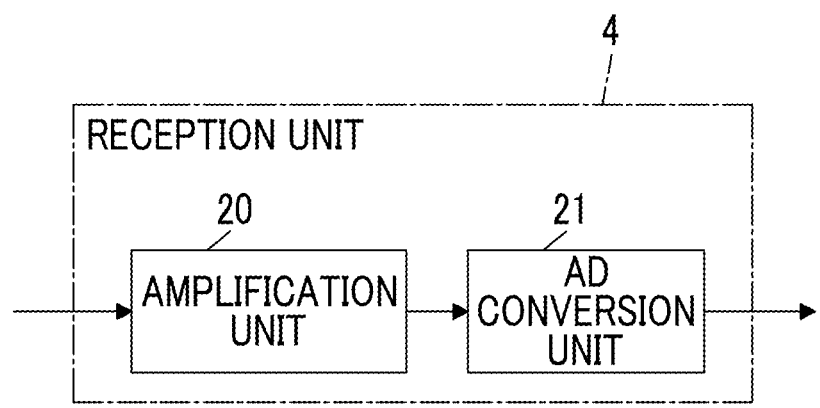
FIG. 2 is a block diagram illustrating an internal configuration of a reception unit in Embodiment 1 of the invention.

The reception unit 4 of the processor 19 processes the reception signals output from the array transducer 2 according to the control signals from the device control unit 12. As illustrated in FIG. 2, the reception unit 4 has a configuration in which an amplification unit 20 and an analog digital (AD) conversion unit 21 are connected in series. The amplification unit 20 amplifies the reception signals input from each element constituting the array transducer 2, and transmits the amplified reception signals to the AD conversion unit 21. The AD conversion unit 21 converts the reception signals transmitted from the amplification unit 20 into digitized data, and sends the data to the image generation unit 5 of the processor 19.

Figure 3:
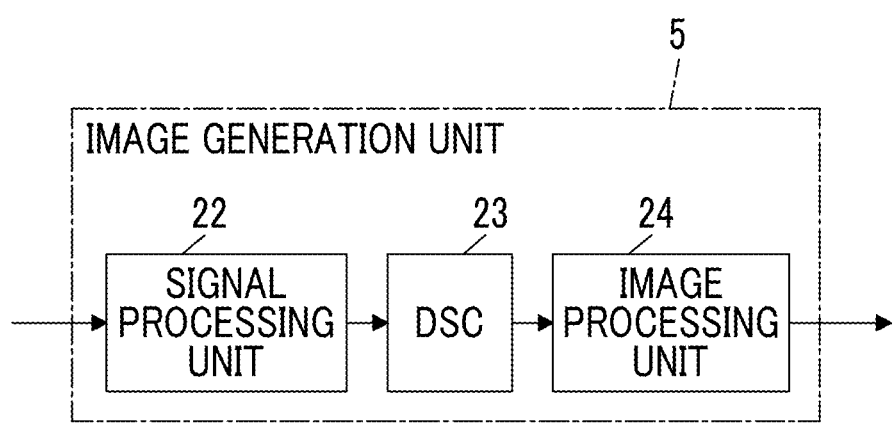
FIG. 3 is a block diagram illustrating an internal configuration of an image generation unit in Embodiment 1 of the invention.

As illustrated in FIG. 3, the image generation unit 5 of the processor 19 has a configuration in which a signal processing unit 22, a digital scan converter (DSC) 23, and an image processing unit 24 are connected in series. The signal processing unit 22 performs reception focusing processing in which addition (phasing addition) is performed by giving delays to respective pieces of element data according to a set sound speed, on the basis of a reception delay pattern selected according to the control signals from the device control unit 12. Through the reception focusing processing, a sound ray signal with narrowed focus of the ultrasound echo is generated. The signal processing unit 22 generates a B mode image signal, which is tomographic image information regarding tissues inside the subject, by performing envelope detection processing after correcting the attenuation of the generated sound ray signal which is caused by the propagation distance according to the depth of the reflection position of the ultrasonic wave. The B mode image signal generated as described above is output to the DSC 23.

The DSC 23 raster-converts the B mode image signal into an image signal according to a normal television signal scanning method. The image processing unit 24 performs various kinds of necessary image processing, such as brightness correction, gradation correction, sharpness correction, and color correction, on the image data obtained in the DSC 23, and then outputs the B mode image signal to the display control unit 6 and the measurement unit 8. The details of the measurement unit 8 will be described below.

The operation unit 16 of the ultrasound diagnostic apparatus 1 is for the user to perform an input operation, and can be configured to comprise a keyboard, a mouse, a trackball, a touchpad, a touch panel, and the like.

The measurement item designation acceptance unit 13 of the processor 19 accepts designation of the measurement item relating to the measurement target from the user through the operation unit 16.

The measurement item relating to the measurement target is an item that can indicate at least one of the measurement target or the measurement content, and the measurement target can include items relating to the name of a target site such as an organ, the name of a lesion such as a tumor, a cyst, bleeding, and abnormalities. In addition, the measurement content can include the length, the area, and the like of the measurement target. Therefore, for example, the measurement item can include any one of only the name of the measurement target, only the name of the lesion, only the item relating to the abnormalities, the name of the measurement target and the measurement content thereof, the name of the lesion and the measurement content thereof, and the item relating to the abnormalities and the measurement content thereof. In a case where the measurement item includes only the measurement target, for example, the measurement content such as whether to measure the length or whether to measure the size is associated with the measurement target designated by the user through the operation unit 16. Specifically, for example, a table in which the measurement target and the measurement content are associated with each other is stored in the storage unit 17 or an external memory (not illustrated), and the measurement content corresponding to the measurement target is selected on the basis of the table.

The position designation acceptance unit 14 of the processor 19 accepts designation of the position of the measurement target on the ultrasound image displayed on the display unit 7, from the user through the operation unit 16.

The user identification information acceptance unit 15 of the processor 19 accepts user identification information input from the user through the operation unit 16. Here, the user identification information is information for identifying a user, which is allocated to each user who uses the ultrasound diagnostic apparatus 1, and can be set in advance by being input by the user through the operation unit 16. For example, as the user identification information, a user identification data (ID), a user's name, an employee number, an email address, a login name, or the like can be used.

The detection and measurement algorithm setting unit 9 of the processor 19 sets an algorithm for detecting the measurement target and an algorithm for measuring the measurement target on the basis of the measurement item that the measurement item designation acceptance unit 13 has accepted from the user through the operation unit 16. Generally, the algorithm for detecting the measurement target on the image differs depending on the kind of the measurement target such as organs and lesions. In addition, the algorithm for measuring the measurement target on the image differs depending on the measurement content such as measuring of the length and measuring of the area of the measurement target. The detection and measurement algorithm setting unit 9 stores a table in which algorithms corresponding to respective measurement targets and algorithms corresponding to respective measurement contents are associated with each other, and sets a detection and measurement algorithm with reference to the table in which the algorithms are associated in a case where the measurement item designation acceptance unit 13 accepts the measurement item from the user through the operation unit 16.

As the detection and measurement algorithm, a well-known algorithm that is generally used can be used. Here, the algorithm defines a calculation unit for achieving the purpose such as detection and measurement, and for example, the algorithm is implemented as a software program in an apparatus and is executed by a central processing unit (CPU).

For example, for the algorithm for detecting the measurement target, there is a method of storing typical pattern data in advance as a template, calculating a similarity for the pattern data while searching an image with a template, and considering that a measurement target is present at a location where the similarity is equal to or greater than a threshold value and is the maximum. For the calculation of the similarity, in addition to simple template matching, for example, a machine learning method described in Csurka et al.: Visual Categorization with Bags of Keypoints, Proc. of ECCV Workshop on Statistical Learning in Computer Vision, pp. 59-74 (2004) or a general image recognition method using deep learning described in Krizhevsk et al.: ImageNet Classification with Deep Convolutional Neural Networks, Advances in Neural Information Processing Systems 25, pp. 1106-1114 (2012) can be used.

In a case where the position designation acceptance unit 14 has accepted the designation of the position of the measurement target from the user through the operation unit 16, the measurement unit 8 of the processor 19 detects the measurement target on the basis of the accepted position and the detection and measurement algorithm set by the detection and measurement algorithm setting unit 9 and measures the detected measurement target to cause the display unit 7 to display the measurement result including the measurement point. Here, in case of detecting the measurement target, the measurement unit 8 detects the measurement target by scanning a detection region in the scan range set on the ultrasound image on the basis of the detection and measurement algorithm. The detection region is a region for searching for the measurement target. Further, as will be described below, in a case where the scan range is modified by the scan range modification unit 10, the measurement unit 8 detects the measurement target by scanning the detection region in the modified scan range.

The scan range modification unit 10 of the processor 19 modifies at least one of the size or position of the scan range, which is used in a case where the measurement unit 8 detects the measurement target on the basis of the position designated by the user through the operation unit 16, and sends information on the modified scan range to the scan range memory 11.

The scan range memory 11 stores the scan range modified by the scan range modification unit 10 for each user ID accepted by the user identification information acceptance unit 15. The scan range stored for each user in this manner is used in a case where the measurement unit 8 detects the measurement target.

Here, as the scan range memory 11, recording media such as a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server, or the like can be used.

The device control unit 12 of the processor 19 controls each unit of the ultrasound diagnostic apparatus 1 on the basis of the program stored in advance in the storage unit 17 or the like and the user's operation through the operation unit 16.

The display control unit 6 of the processor 19 performs predetermined processing on a B mode image generated by the image generation unit 5, the measurement result obtained by the measurement unit 8, the information on the scan range modified by the scan range modification unit 10, and the like to cause the display unit 7 to display the B mode image, the measurement result, the information on the scan range, and the like under the control of the device control unit 12.

The display unit 7 of the ultrasound diagnostic apparatus 1 displays an image or the like under the control of the display control unit 6, and includes, for example, a display device such as a liquid crystal display (LCD).

The storage unit 17 stores an operation program and the like of the ultrasound diagnostic apparatus 1, and as in the scan range memory 11 of the ultrasound diagnostic apparatus 1, recording media such as an HDD, an SSD, an FD, an MO disc, an MT, a RAM, a CD, a DVD, an SD card, and an USB memory, a server, or the like can be used as the storage unit 17.

The processor 19 having the transmission unit 3, the reception unit 4, the image generation unit 5, the display control unit 6, the measurement unit 8, the detection and measurement algorithm setting unit 9, the scan range modification unit 10, the device control unit 12, the measurement item designation acceptance unit 13, the position designation acceptance unit 14, and the user identification information acceptance unit 15 is configured by a CPU and a control program causing the CPU to execute various kinds of processing, but may be configured by a digital circuit. In addition, the transmission unit 3, the reception unit 4, the image generation unit 5, the display control unit 6, the measurement unit 8, the detection and measurement algorithm setting unit 9, the scan range modification unit 10, the device control unit 12, the measurement item designation acceptance unit 13, the position designation acceptance unit 14, and the user identification information acceptance unit 15 can also be configured by being integrated partially or entirely into one CPU.

Figure 4:
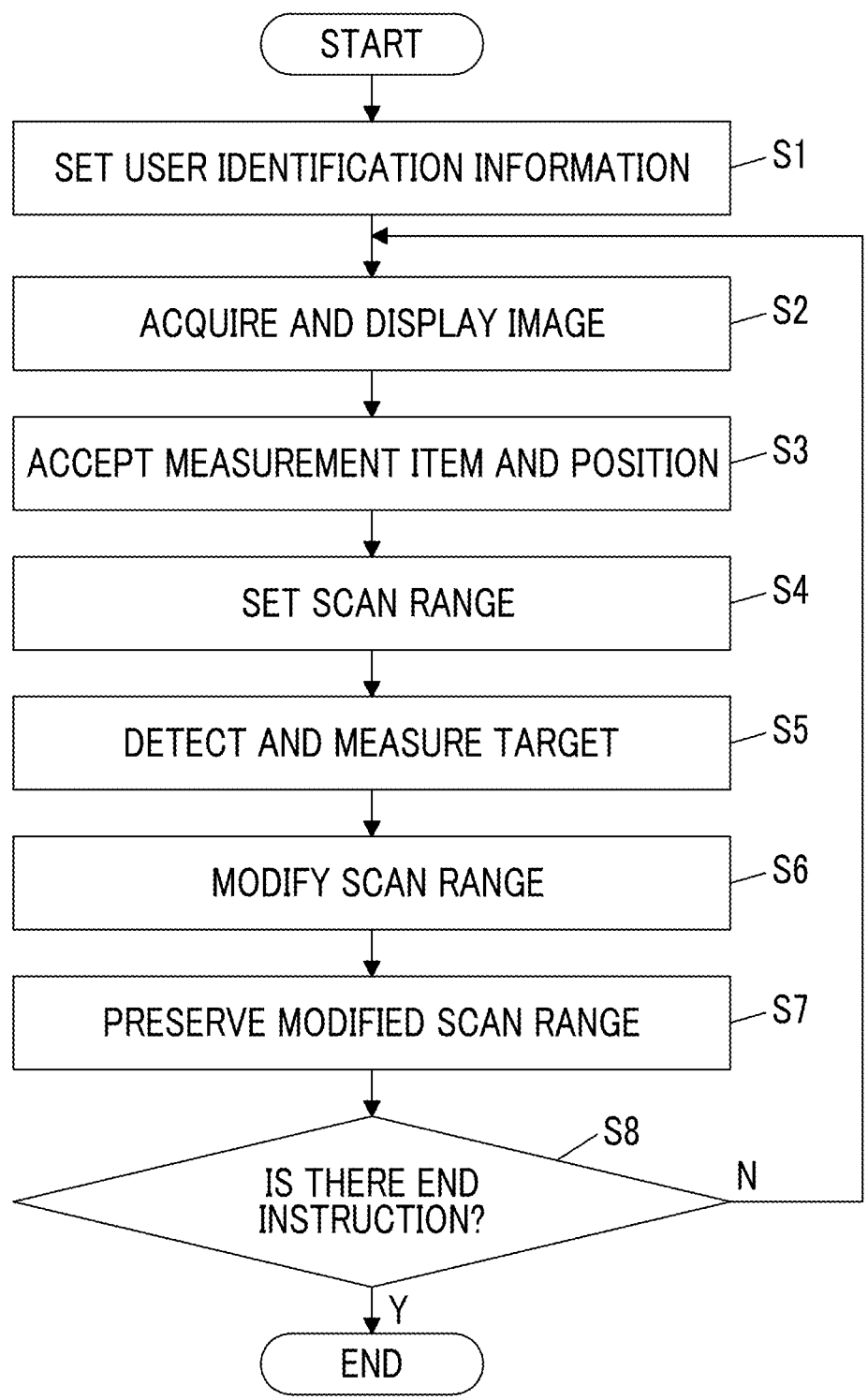
FIG. 4 is a flowchart illustrating an operation of the ultrasound diagnostic apparatus according to Embodiment 1 of the invention.

Next, the measurement operation of the ultrasound diagnostic apparatus 1 according to Embodiment 1 will be described with reference to the flowchart illustrated in FIG. 4.

First, in step S1, the user identification information acceptance unit 15 accepts the user identification information input from the user through the operation unit 16. For example, in this case, the user can directly input the user identification information to the ultrasound diagnostic apparatus 1 through the operation unit 16 such as a keyboard. In addition, for example, the user identification information input in the past diagnosis is stored in the storage unit 17 or the like, and a list of the user identification information stored in the storage unit 17 or the like is displayed on the display unit 7 in a case where the operation of the ultrasound diagnostic apparatus 1 is started so that the user can select one of a plurality of pieces of the user identification information displayed in a list through the operation unit 16.

Next, in step S2, an ultrasound image is acquired, and the acquired ultrasound image is displayed on the display unit 7. As the ultrasound image, an image captured on the spot using the probe 18 can be used. Further, the past ultrasound image stored in an image memory (not illustrated) or the like can be used.

Figure 5:
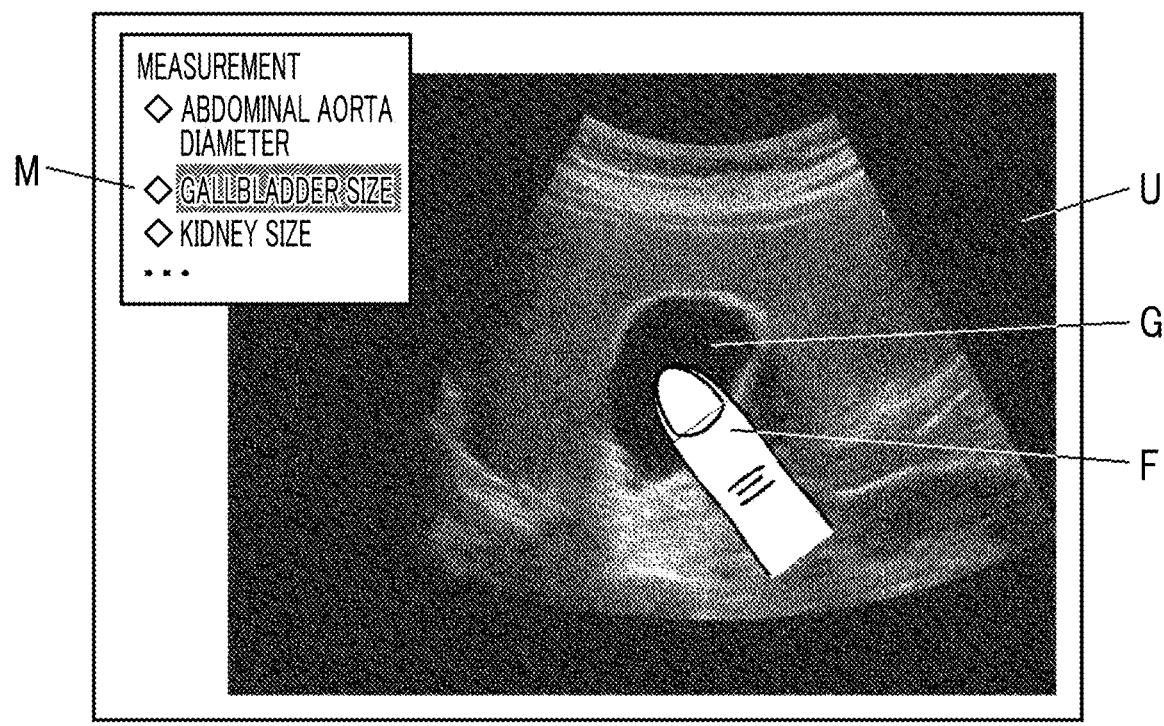
FIG. 5 is a schematic diagram illustrating an aspect in which a user designates a measurement item and a measurement position.

In subsequent step S3, the measurement item and the measurement position on the ultrasound image designated from the user through the operation unit 16 are respectively accepted by the measurement item designation acceptance unit 13 and the position designation acceptance unit 14. Here, in a case where the user designates the measurement item, for example, as illustrated in FIG. 5, a list M of the measurement items is displayed on the display unit 7 so that the user can select one of the plurality of measurement items displayed in the list M through the operation unit 16. In the example illustrated in FIG. 5, the gallbladder size is selected as the measurement item. The measurement item designation acceptance unit 13 accepts the measurement item designated by the user in this manner. In a case where the measurement item is accepted, a detection and measurement algorithm according to the measurement item is set by the detection and measurement algorithm setting unit 9.

Further, the user designates one point in a region representing the measurement target in case of designating the measurement position on the ultrasound image. For example, in a case where the display unit 7 is a display with a touch panel and the operation unit 16 is configured by the touch panel of the display unit 7, as illustrated in FIG. 5, the user can designate the measurement position by touching one point in a region representing a gallbladder G on the ultrasound image. The position designation acceptance unit 14 accepts the measurement position designated by the user in this manner.

Figure 6:
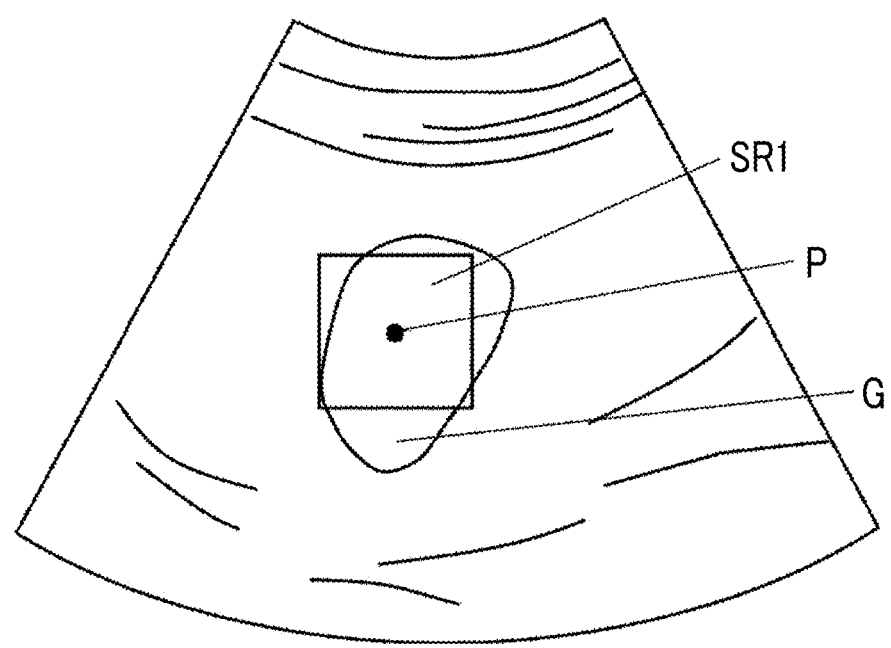
FIG. 6 is a schematic diagram illustrating a set scan range.

In subsequent step S4, as illustrated in FIG. 6, the measurement unit 8 sets a scan range SR1 centered on a measurement position P designated by the user in step S3. The size of the scan range SR1 can be set in advance. In the example illustrated in FIG. 6, the shape of the scan range SR1 is a rectangle, but the shape is not particularly limited and may be a circle or the like.

Figure 7:
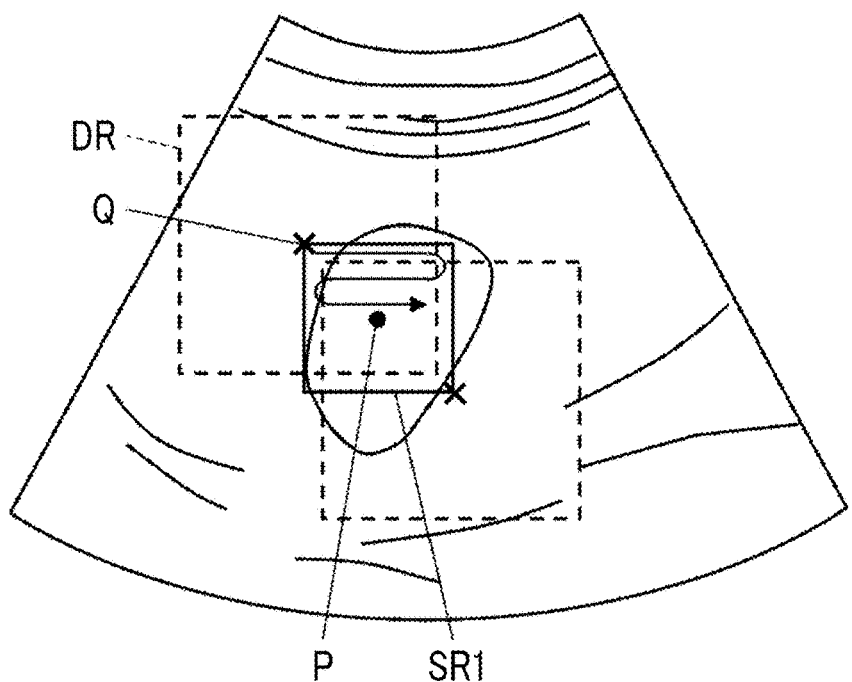
FIG. 7 is a schematic diagram illustrating an aspect of scanning a detection region in the scan range.

In step S5, the measurement unit 8 detects the measurement target by scanning a detection region for detecting the measurement target in the scan range SR1 set in step S4 and measures the detected measurement target on the basis of the detection and measurement algorithm set by the detection and measurement algorithm setting unit 9. In case of detecting the measurement target, the measurement unit 8 scans a detection region DR for detecting the measurement target while moving a center Q1 of the detection region DR in the scan range SR1 as illustrated in FIG. 7. In this case, for example, the measurement unit 8 performs an image analysis on each detection region DR to calculate the reliability of the detection of the measurement target, and determines that the measurement target is detected in a case where the reliability is equal to or greater than a certain value. Here, the reliability of the detection of the measurement target is the likelihood of the measurement target in the detection region DR, and for example, the similarity between the template of the measurement target stored in advance as the detection and measurement algorithm and the pattern in the detection region DR can be used as the reliability of the detection of the measurement target.

Figure 8:
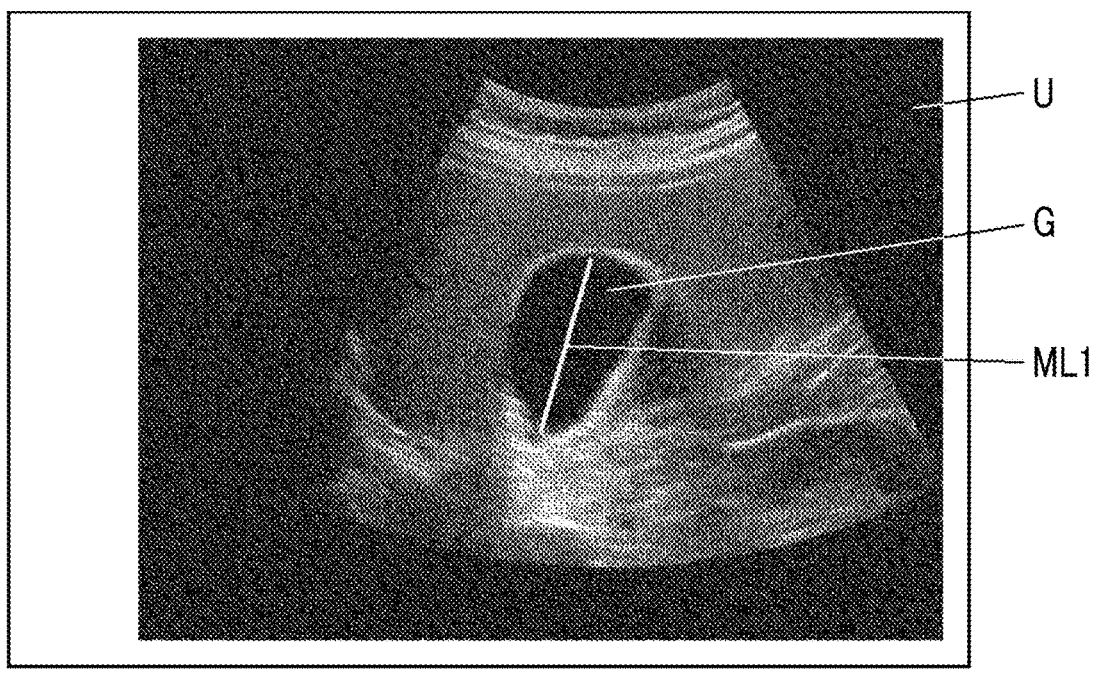
FIG. 8 is a diagram illustrating a measurement line disposed on an ultrasound image.

In a case where the measurement target is detected in this manner, the measurement unit 8 measures the measurement target on the basis of a rule determined according to the measurement item by the detection and measurement algorithm, and causes the display unit 7 to display the obtained measurement result. For example, in a case where the measurement item is the gallbladder size, as illustrated in FIG. 8, the measurement unit 8 sets the longest line segment among line segments, of which the end points are two measurement points disposed on the inner wall of the region representing the gallbladder G, as a measurement line ML1 to measure the length of the measurement line ML1, and causes the display unit 7 to display the measurement result including the measurement line ML1.

Figure 9:
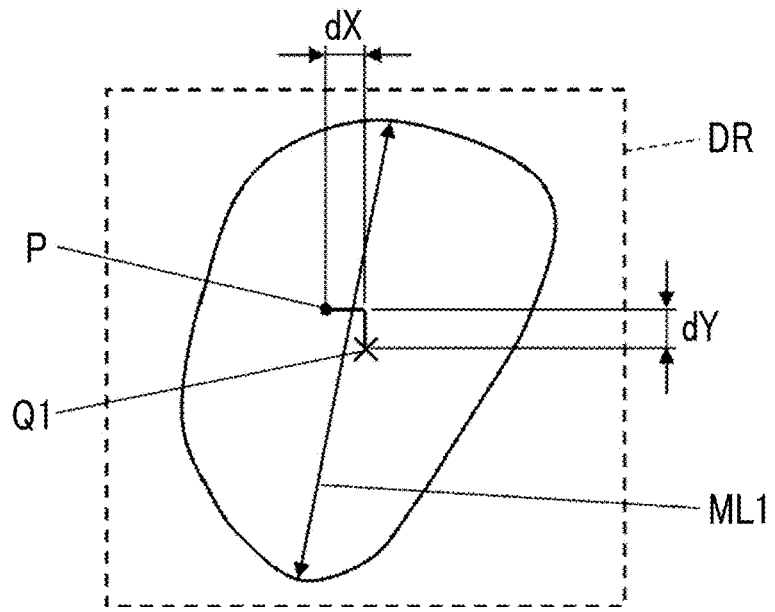
FIG. 9 is a schematic diagram illustrating a deviation amount of the scan range in Embodiment 1 of the invention.

In subsequent step S6, the scan range modification unit 10 modifies the scan range SR1 set in step S4 on the basis of the measurement position designated by the user in step S3 and the detection result of the measurement target in step S5. In this case, the scan range modification unit 10 calculates a deviation amount of the scan range SR1. Here, the deviation amount of the scan range SR1 is deviation amounts dX and dY between the measurement position P designated by the user in step S3 and the center Q1 of the detection region DR in which the measurement target is detected in step S5 as illustrated in FIG. 9. Here, for example, the scan range modification unit 10 can use a detection region DR having the maximum reliability of detection of the measurement target, as the detection region DR in which the measurement target is detected.

Figure 10:
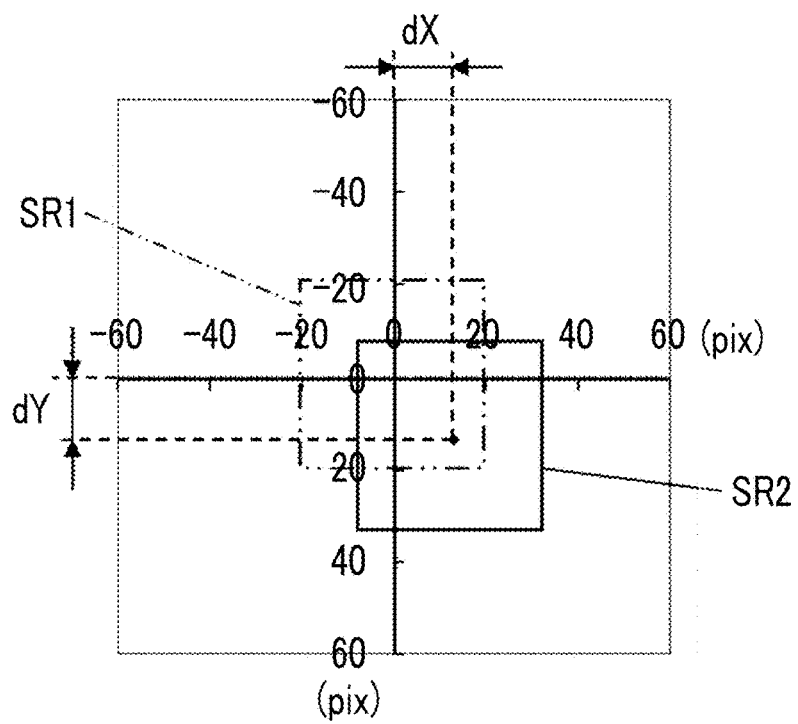
FIG. 10 is a diagram illustrating an example of a modified scan range in Embodiment 1 of the invention.

The scan range modification unit 10 calculates a modification amount of the scan range SR1 on the basis of the deviation amounts dX and dY of the scan range SR1, and modifies at least one of the size or position of the scan range SR1 on the basis of the modification amount. For example, as illustrated in FIG. 10, the scan range modification unit 10 sets the deviation amounts dX and dY of the scan range SR1 as the modification amount, and modifies the scan range SR1 to a scan range SR2 which is translated parallel by the deviation amounts dX and dY. In this manner, the scan range SR1 can be modified to the scan range SR2 in which the tendency of the measurement position designated by the user is reflected.

In subsequent step S7, the scan range modification unit 10 stores the scan range modified in step S6, in the scan range memory 11.

In step S8, it is determined whether there is an end instruction for the measurement operation of the ultrasound diagnostic apparatus 1. Here, in a case where there is no end instruction for the measurement operation of the ultrasound diagnostic apparatus 1, the processing returns to step S2, and an ultrasound image is acquired and the ultrasound image is displayed on the display unit 7. Next, in subsequent step S3, the measurement item and the measurement position designated by the user through the operation unit 16 are accepted, and the detection and measurement algorithm is set according to the measurement item.

In step S4, the measurement unit 8 sets the scan range SR2 modified by the scan range modification unit 10 in step S11 on the ultrasound image on the basis of the set detection and measurement algorithm. In subsequent step S5, the measurement unit 8 detects the measurement target by scanning the detection region DR in the scan range SR2, and measures the detected measurement target.

In step S6, the scan range modification unit 10 further modifies the scan range SR2 on the basis of the measurement position designated by the user in step S3. In subsequent step S7, a new scan range obtained by modifying the scan range SR2 is stored in the scan range memory 11.

In this manner, until there is an end instruction for the measurement operation of the ultrasound diagnostic apparatus 1 in step S8, the processing of step S2 to step S8 is repeated, and the scan range for detecting the measurement target is modified one after another. In a case where there is an end instruction for the measurement operation of the ultrasound diagnostic apparatus 1 in step S8, the operation of the ultrasound diagnostic apparatus 1 is ended.

As described above, with the ultrasound diagnostic apparatus 1 of Embodiment 1, since the scan range for detecting the measurement target is modified by adding the measurement position designated by the user through the operation unit 16 for each piece of the user identification information and the detection of the measurement target is performed from the next time using the modified scan range, it is possible to easily and accurately perform detection and measurement of the measurement target regardless of the user.

Figure 11:
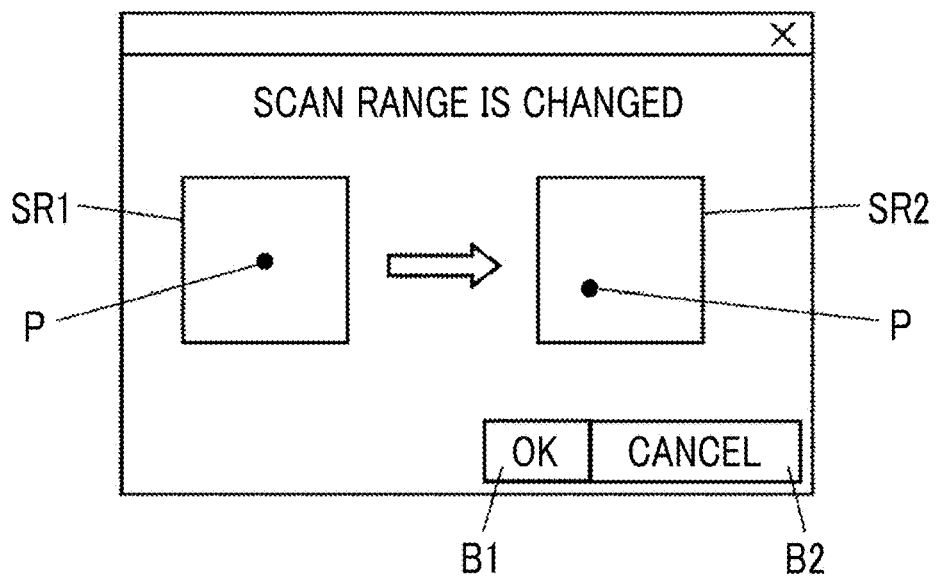
FIG. 11 is a diagram illustrating an example of a display for notifying a user that a scan range will be changed.

Although not illustrated, the ultrasound diagnostic apparatus 1 can be provided with a scan range change notification unit that notifies a user that the scan range is changed. For example, as illustrated in FIG. 11, the scan range change notification unit causes the display unit 7 to display a text indicating the scan range SR1 is changed to the scan range SR2 and a positional relationship between the scan ranges SR1 and SR2 and the measurement position P designated by the user. Further, the scan range change notification unit can cause the display unit 7 to display an OK button B1 and a cancel button B2 for causing the user to select whether to change the scan range SR1 to the scan range SR2, together with the fact that the scan range is changed.

Although not illustrated, the ultrasound diagnostic apparatus 1 may be provided with a sound generation unit including a speaker and the like, and the scan range change notification unit may perform a notification indicating the scan range is changed using a sound through the sound generation unit.

In this manner, the fact that the scan range SR1 is changed is notified to the user so that it is possible for the user to grasp the range on the ultrasound image to be scanned by the measurement unit 8.

Embodiment 2

In Embodiment 1, the scan range is modified each time the measurement of the measurement target is performed, but the scan range can be modified each time the measurement is performed a plurality of times. Here, the ultrasound diagnostic apparatus 1 of Embodiment 2 is the same as the ultrasound diagnostic apparatus 1 of Embodiment 1 illustrated in FIG. 1, and in the measurement operation of the ultrasound diagnostic apparatus 1 of Embodiment 2, the scan range modifying processing in step S6 in the flowchart illustrated in FIG. 4 is replaced with the flowchart illustrated in FIG. 12.

In step S1, user inputs user identification information through the operation unit 16, and the user identification information acceptance unit 15 accepts the user identification information input from the user.

Next, in step S2, an ultrasound image is acquired, and the acquired ultrasound image is displayed on the display unit 7.

In step S3, in a case where the measurement item is designated by the user through the operation unit 16 and the measurement item is accepted by the measurement item designation acceptance unit 13, a detection and measurement algorithm is set by the detection and measurement algorithm setting unit 9 according to the measurement item. Further, in step S3, the measurement position on the ultrasound image is designated through the operation unit 16, and the measurement position is accepted by the position designation acceptance unit 14.

In step S4, the scan range SR1 is set by the measurement unit 8 on the basis of the detection and measurement algorithm. In subsequent step S5, the measurement unit 8 detects the measurement target by performing the scanning in the scan range SR1 set in step S4, and measures the detected measurement target on the basis of the detection and measurement algorithm. In a case where the processing in step S5 is completed in this manner, the processing proceeds to step S9.

In step S9, the scan range modification unit 10 calculates the deviation amounts dX and dY of the scan range SR1, and stores the calculated deviation amounts dX and dY in the scan range memory 11 for each piece of the user identification information.

In subsequent step S10, the scan range modification unit 10 determines whether data of the deviation amounts dX and dY corresponding to N times of measurement, which is a predetermined number of times, that is, N sets of deviation amounts dX and dY are stored in the scan range memory 11 for the same user identification information. Here, in a case where N sets of deviation amounts dX and dY are not yet stored in the scan range memory 11, the processing of step S6 is completed without modifying the scan range SR1, and the processing proceeds to step S7.

In step S7, the scan range modification unit 10 stores the scan range modified in step S6, in the scan range memory 11. Here, in a case where N sets of deviation amounts dX and dY are not stored in the scan range memory 11 and thus the scan range SR1 is not modified, the scan range modification unit 10 does not store a new scan range in the scan range memory 11, and the processing proceeds to step S8.

In step S8, it is determined whether there is an end instruction for the measurement operation of the ultrasound diagnostic apparatus 1. Here, in a case where there is no end instruction, the processing returns to step S2, and an ultrasound image is acquired and the ultrasound image is displayed on the display unit 7. For the new ultrasound image acquired in step S2, in a case where a measurement item and a measurement position are accepted, a scan range SR1 is set, and the measurement target is detected and measured in subsequent step S3 to step S5, the processing proceeds to step S9.

In step S9, the scan range modification unit 10 calculates deviation amounts dX and dY of the scan range SR1 from a measurement position P newly designated by the user in step S3 and a position of a center Q1 of a detection region DR in which the measurement target is newly detected in step S5, and stores the calculated deviation amounts dX and dY in the scan range memory 11. In this manner, in a case where there is no end instruction in step S8, processing of step S2 to step S5, step S9, step S10, step S7, and step S8 is repeated until N sets of deviation amounts dX and dY are stored in the scan range memory 11.

Figure 13:
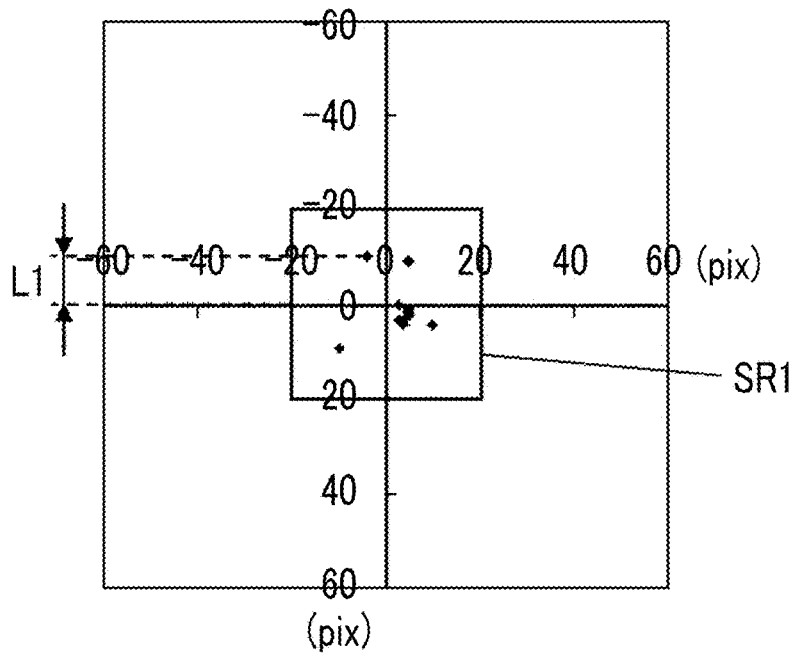
FIG. 13 is a diagram illustrating an example of a distribution of a deviation amount of a scan range.

In a case where the scan range modification unit 10 determines that N sets of deviation amounts dX and dY are stored in the scan range memory 11 in step S10, the processing proceeds to step S11. In step S11, the scan range modification unit 10 calculates a modification amount of the scan range SR1 on the basis of the N sets of deviation amounts dX and dY for the same user identification information. For example, as illustrated in FIG. 13, the scan range modification unit 10 calculates a maximum value L1 of the N sets of deviation amounts dX and dY as the modification amount of the scan range SR1. In the example illustrated in FIG. 13, 10 sets of deviation amounts dX and dY are plotted.

Figure 14:
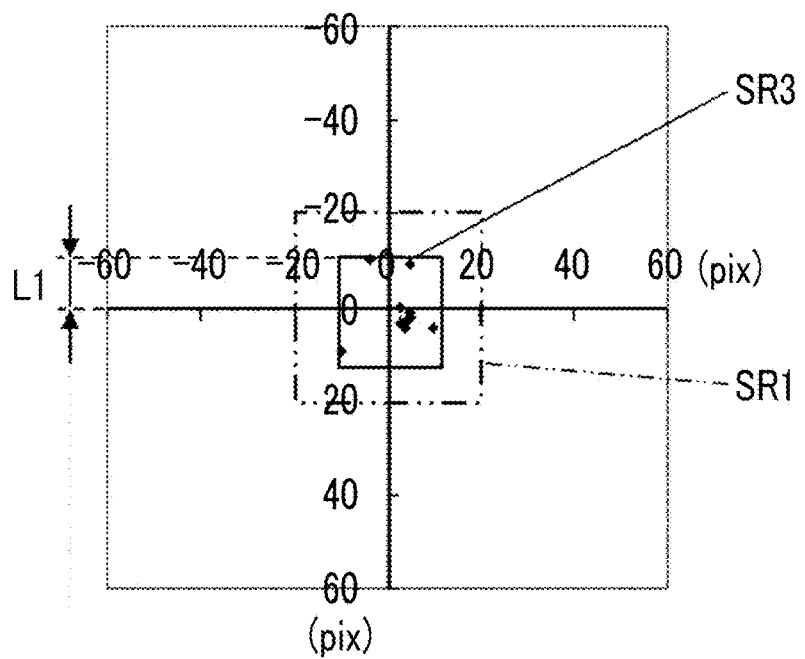
FIG. 14 is a diagram illustrating an example of a modified scan range.

In subsequent step S12, the scan range modification unit 10 modifies the scan range SR1 on the basis of the modification amount calculated in step S11. For example, as illustrated in FIG. 14, the scan range modification unit 10 modifies the scan range SR1 to a scan range SR3 having width of the maximum value L1 of the N sets of deviation amounts dX and dY from the origin. As a result, the scan range SR1 can be modified to the scan range SR3 in which the tendency of the measurement position designated by the user is reflected. In this manner, the scan range is modified each time N sets of deviation amounts dX and dY are stored in the scan range memory 11.

In step S7 subsequent to step S12, the scan range memory 11 stores the scan range SR3 obtained by modifying the scan range SR1.

In a case where there is no end instruction for the measurement operation of the ultrasound diagnostic apparatus 1 in subsequent step S8, the processing returns to step S2 again. In a case where there is an end instruction for the measurement operation of the ultrasound diagnostic apparatus 1 in step S8, the operation of the ultrasound diagnostic apparatus 1 is ended.

With the ultrasound diagnostic apparatus 1 of Embodiment 2, since the scan range is modified on the basis of statistical data consisting of a plurality of sets of deviation amounts of the scan range, it is possible to modify the scan range by more accurately reflecting the tendency of the measurement position designated by the user.

In Embodiment 2, the scan range modification unit 10 calculates the maximum value L1 among a plurality of sets of deviation amounts dX and dY of the scan range SR1 as the modification amount for modifying the scan range SR1, but the invention is not limited thereto. For example, in a case where the maximum value L1 among a plurality of sets of deviation amounts dX and dY is set to 100%, the scan range modification unit 10 can calculate a value having a size of upper K % as the modification amount. In addition, the scan range modification unit 10 can calculate a value having the J-th size counting from the maximum value L1 among a plurality of sets of deviation amounts dX and dY, as the modification amount.

The scan range modification unit 10 can calculate an average value of a plurality of deviation amounts dX and dY or a value obtained by adding a certain number to the average value as the modification amount. As a result, it is possible to prevent that an extremely large value and an extremely small value among a plurality of deviation amounts dX and dY are calculated as the modification amount.

In addition, the scan range modification unit 10 can set a value obtained by multiplying the value calculated as the modification amount by a certain number, as the final modification amount.

Figure 15:
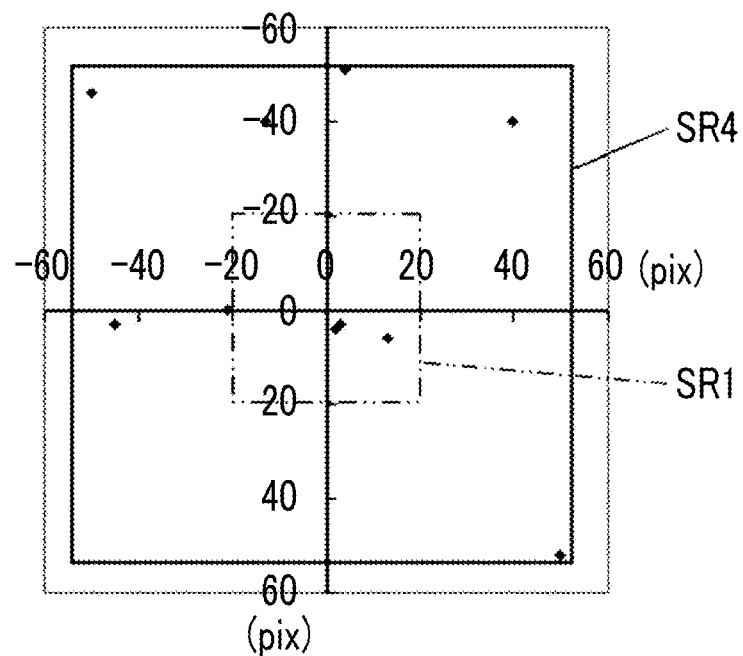
FIG. 15 is a diagram illustrating another example of a modified scan range.

In Embodiment 2, the scan range SR1 having a size set in advance is modified to obtain the scan range SR3 smaller than the scan range SR1, but a scan range obtained by modifying the scan range SR1 may have various sizes depending on the value of a plurality of deviation amounts dX and dY of the scan range SR1. For example, in a case where a plurality of sets of deviation amounts dX and dY are distributed in a wider range than the scan range SR1 as illustrated in FIG. 15, a scan range SR4 larger than the scan range SR1 can be obtained.

Figure 16:
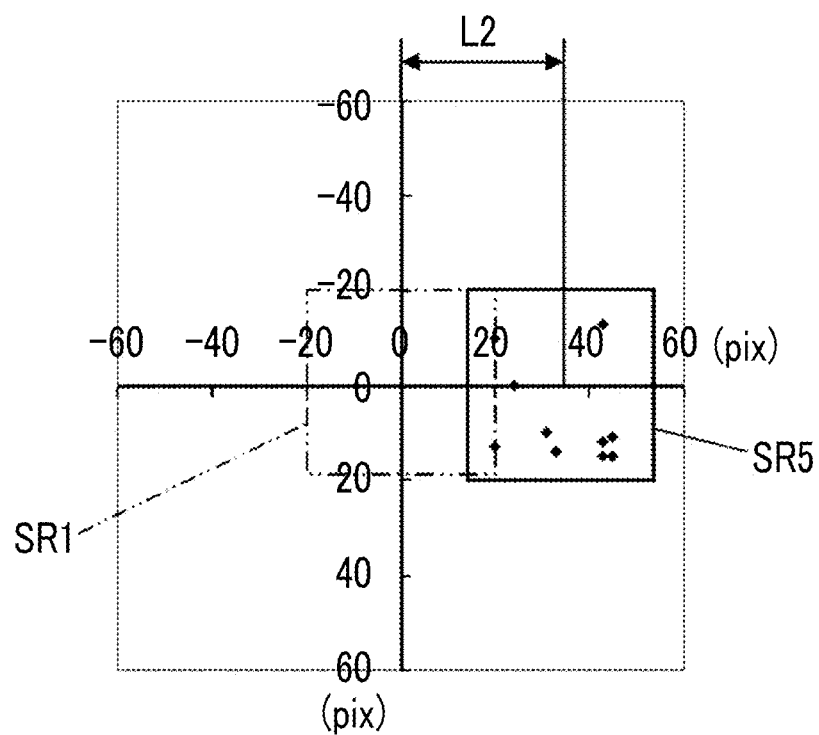
FIG. 16 is a diagram illustrating still another example of a modified scan range.
Figure 17:
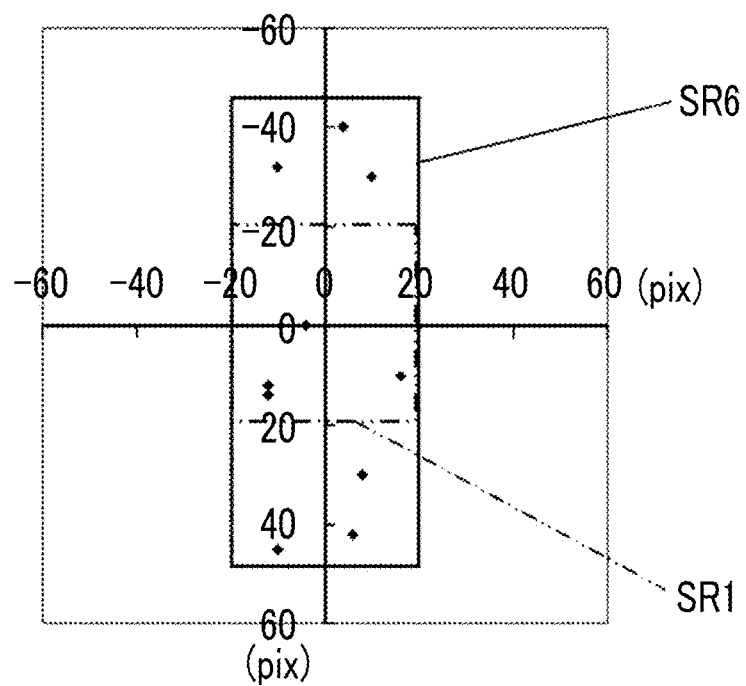
FIG. 17 is a diagram illustrating still another example of a modified scan range.

In addition, in Embodiment 2, the scan range modification unit 10 calculates the maximum value L1 among a plurality of sets of deviation amounts dX and dY of the scan range SR1 as the modification amount, and modifies the scan range SR1 to the scan range SR3 having a width of the length L1 from the origin, but the method of modifying the scan range is not limited thereto. For example, as illustrated in FIG. 16, in a case where the distribution of a plurality of sets of deviation amounts dX and dY is biased, the scan range modification unit 10 can calculate a distance L2 for translating the scan range SR1 parallel such that the scan range SR1 includes all of the plurality of sets of deviation amounts dX and dY, as the modification amount, and modify the scan range SR1 to a scan range SR5 which is translated parallel by the distance L2.

Further, the scan range modification unit 10 can calculate an expansion rate or a reduction rate in a specific direction with respect to the scan range SR1 as the modification amount, and modify the scan range SR1 to a scan range SR6 which is obtained by expanding the range in the specific direction so as to include all of the plurality of sets of deviation amounts dX and dY.

In Embodiment 2, the scan range modification unit 10 calculates the modification amount on the basis of N sets of deviation amounts dX and dY of the scan range SR1 and modifies the scan range SR1, but the number of sets of N sets of deviation amounts dX and dY required for calculating the modification amount can be changed according to the measurement target. For example, the scan range modification unit 10 can change the number of sets of N sets of deviation amounts dX and dY required for calculating the modification amount according to the measurement item accepted by the measurement item designation acceptance unit 13.

In addition, the scan range modification unit 10 can change the number of sets of N sets of deviation amounts dX and dY required for calculating the modification amount by the user's operation through the operation unit 16.

Embodiment 3

Figure 18:
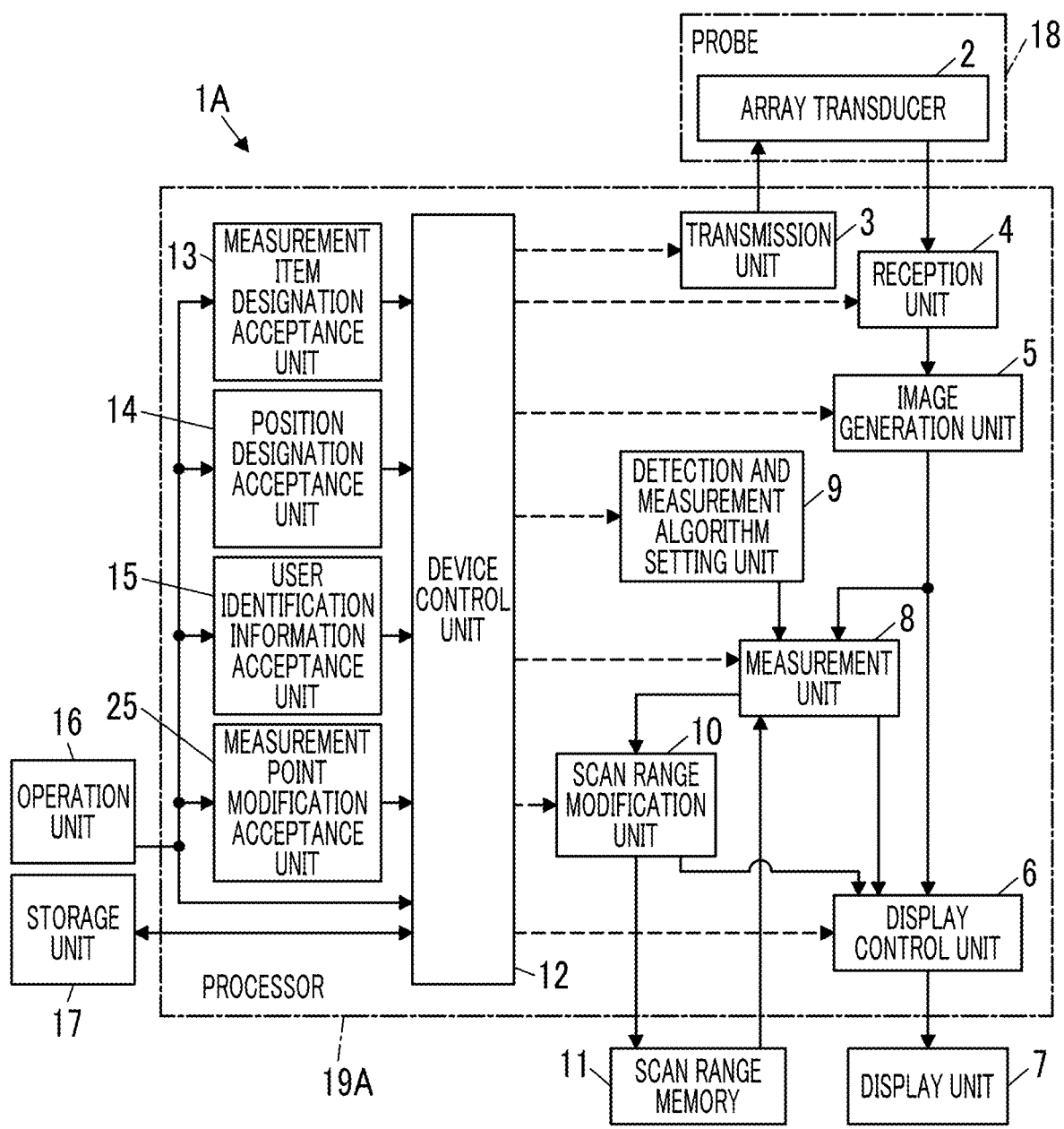
FIG. 18 is a block diagram illustrating a configuration of an ultrasound diagnostic apparatus according to Embodiment 3 of the invention.

In Embodiments 1 and 2, in a case where the measurement item and the measurement position on the ultrasound image are designated by the user, the measurement unit 8 automatically measures the measurement target so that the measurement result is obtained, but the measurement result can be modified by the user through the operation unit 16. FIG. 18 illustrates a configuration of an ultrasound diagnostic apparatus 1A according to Embodiment 3. The ultrasound diagnostic apparatus 1A is obtained by further providing a measurement point modification acceptance unit 25 to the ultrasound diagnostic apparatus 1 of Embodiment 1 illustrated in FIG. 1. As in the measurement item designation acceptance unit 13, the position designation acceptance unit 14, and the user identification information acceptance unit 15, the measurement point modification acceptance unit 25 is connected to the device control unit 12 and the operation unit 16.

In addition, the transmission unit 3, the reception unit 4, the image generation unit 5, the display control unit 6, the measurement unit 8, the detection and measurement algorithm setting unit 9, the scan range modification unit 10, the device control unit 12, the measurement item designation acceptance unit 13, the position designation acceptance unit 14, the user identification information acceptance unit 15, and the measurement point modification acceptance unit 25 constitute a processor 19A.

The measurement point modification acceptance unit 25 of the processor 19A accepts a modification of the position of the measurement point set on the ultrasound image for the measurement of the measurement target by the measurement unit 8. Here, the modification of the measurement point is performed by a manual operation of the user through the operation unit 16.

Figure 19:
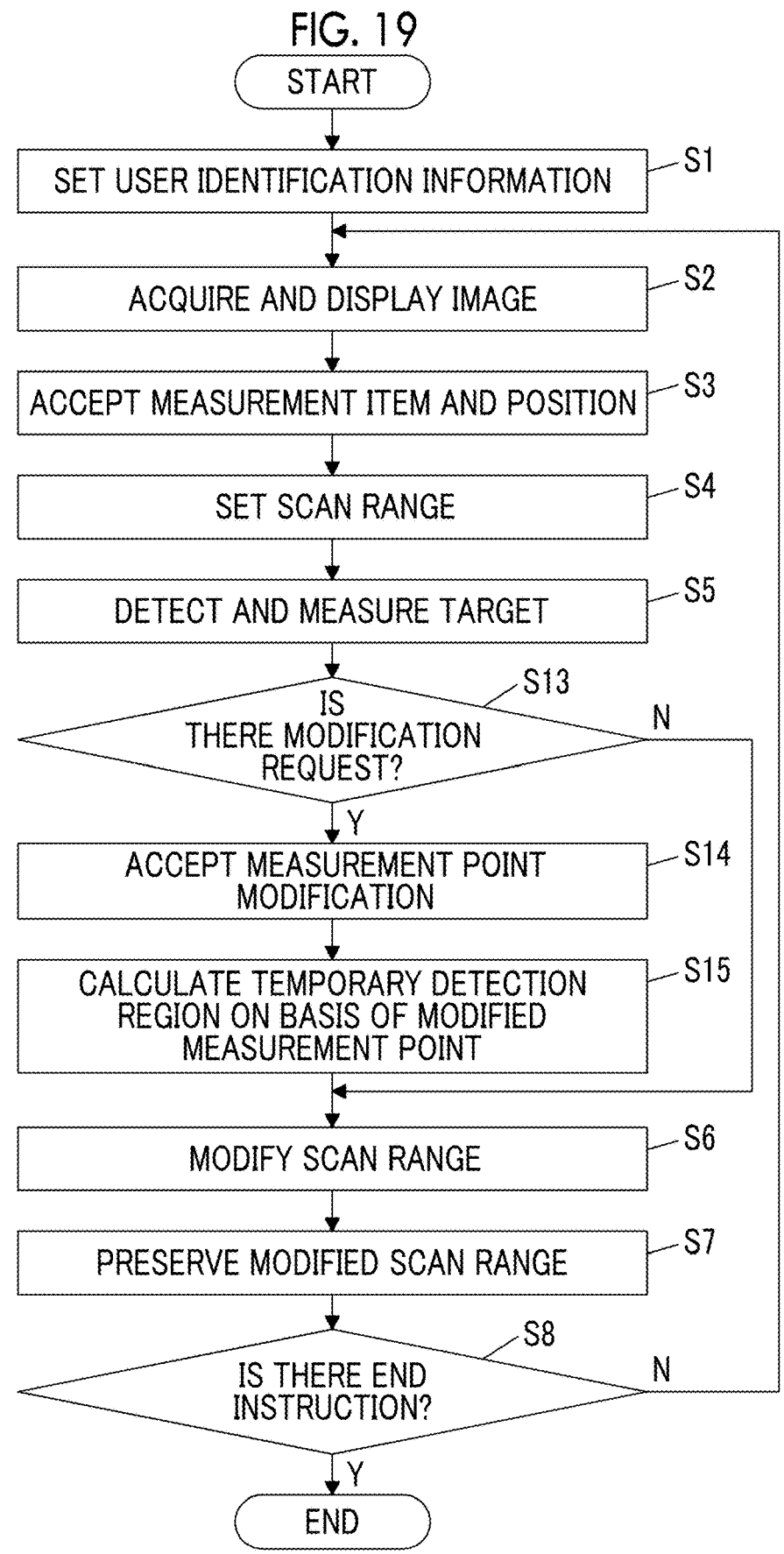
FIG. 19 is a flowchart illustrating an operation of the ultrasound diagnostic apparatus according to Embodiment 3 of the invention.

Next, the measurement operation of the ultrasound diagnostic apparatus 1A according to Embodiment 3 will be described with reference to the flowchart illustrated in FIG. 19. Here, the flowchart illustrated in FIG. 19 is obtained by adding step S13 to step S15 between step S5 and step S6 of the flowchart illustrated in FIG. 4.

In step S1, user inputs user identification information through the operation unit 16, and the user identification information acceptance unit 15 accepts the user identification information input from the user.

Next, in step S2, an ultrasound image is acquired, and the acquired ultrasound image is displayed on the display unit 7.

In step S3, in a case where the measurement item is designated by the user through the operation unit 16 and the measurement item is accepted by the measurement item designation acceptance unit 13, a detection and measurement algorithm is set by the detection and measurement algorithm setting unit 9 according to the measurement item. Further, in step S3, the measurement position on the ultrasound image is designated through the operation unit 16, and the measurement position is accepted by the position designation acceptance unit 14.

In step S4, the scan range SR1 is set by the measurement unit 8 on the basis of the detection and measurement algorithm. In subsequent step S5, the measurement unit 8 detects the measurement target by performing the scanning in the scan range SR1 set in step S4, measures the detected measurement target on the basis of the detection and measurement algorithm, and causes the display unit 7 to display the measurement result. In a case where the processing in step S5 is completed in this manner, the processing proceeds to step S13.

Figure 20:
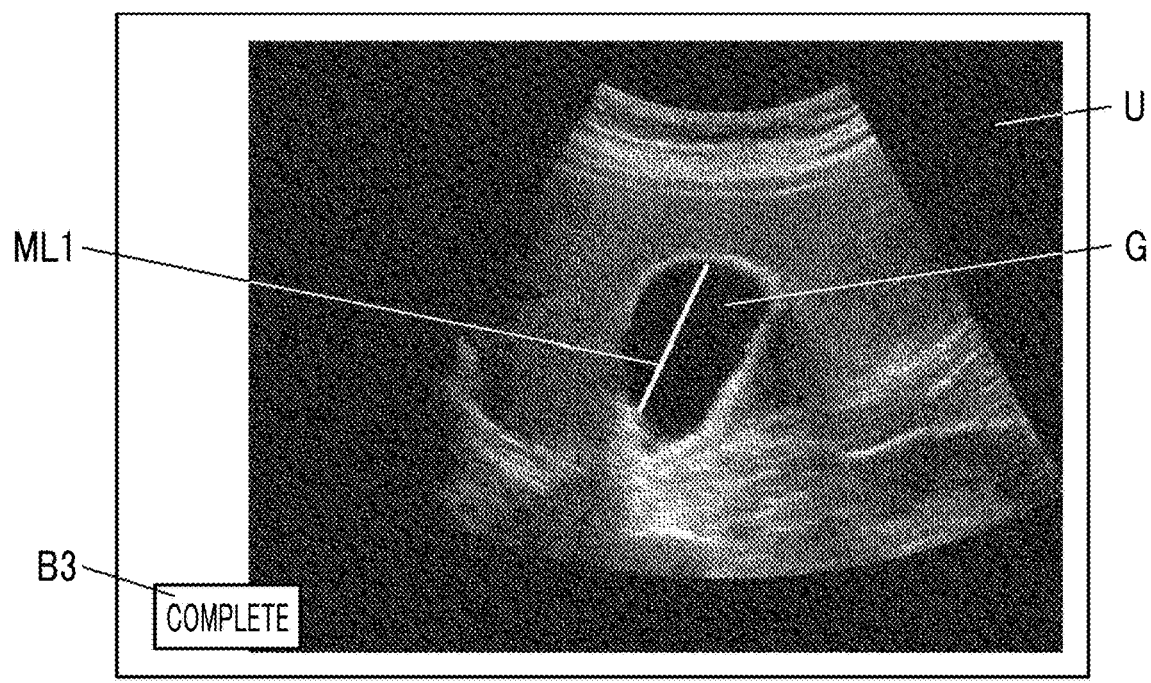
FIG. 20 is a display example of a measurement result obtained by a measurement unit.

In step S13, it is determined whether there is a modification request for the position of the measurement point set on the ultrasound image for performing the measurement in step S5. For example, as illustrated in FIG. 20, a completion button B3 for completing the measurement of the measurement target is displayed on the display unit 7 together with the ultrasound image U and the measurement result such as the measurement line ML1, and in a case where the completion button B3 is pressed by the user through the operation unit 16, it is determined that there is no modification request for the position of the measurement point. In this case, the processing proceeds to step S6.

As illustrated in FIG. 9, in step S6, the scan range modification unit 10 calculates the modification amount of the scan range SR1 from the measurement position P designated by the user in step S3 and the center Q1 of the detection region DR in which the measurement target is detected in step S5, and modifies the scan range SR1.

In step S7, the scan range memory 11 stores a new scan range obtained by the modification of the scan range SR1 in step S6 for each piece of user identification information set in step S1.

In subsequent step S8, it is determined whether there is an end instruction for the measurement operation of the ultrasound diagnostic apparatus 1A. Here, in a case where there is no end instruction for the measurement operation of the ultrasound diagnostic apparatus 1A, the processing returns to step S2, and the processing of step S2 to step S5, step S13, and step S6 to step S8 is performed again as long as there is no modification request for the measurement point in step S13.

In addition, in a case where there is an end instruction for the measurement operation of the ultrasound diagnostic apparatus 1A in step S8, the operation of the ultrasound diagnostic apparatus 1A is ended.

In a case where it is determined that there is a modification request for the measurement point in step S13, the processing proceeds to step S14. For example, in a case where the user changes an end point of the measurement line ML1, that is, the position of the measurement point through the operation unit 16 without pressing the completion button B3 illustrated in FIG. 20, it is determined that there is a modification request for the measurement point.

Figure 21:
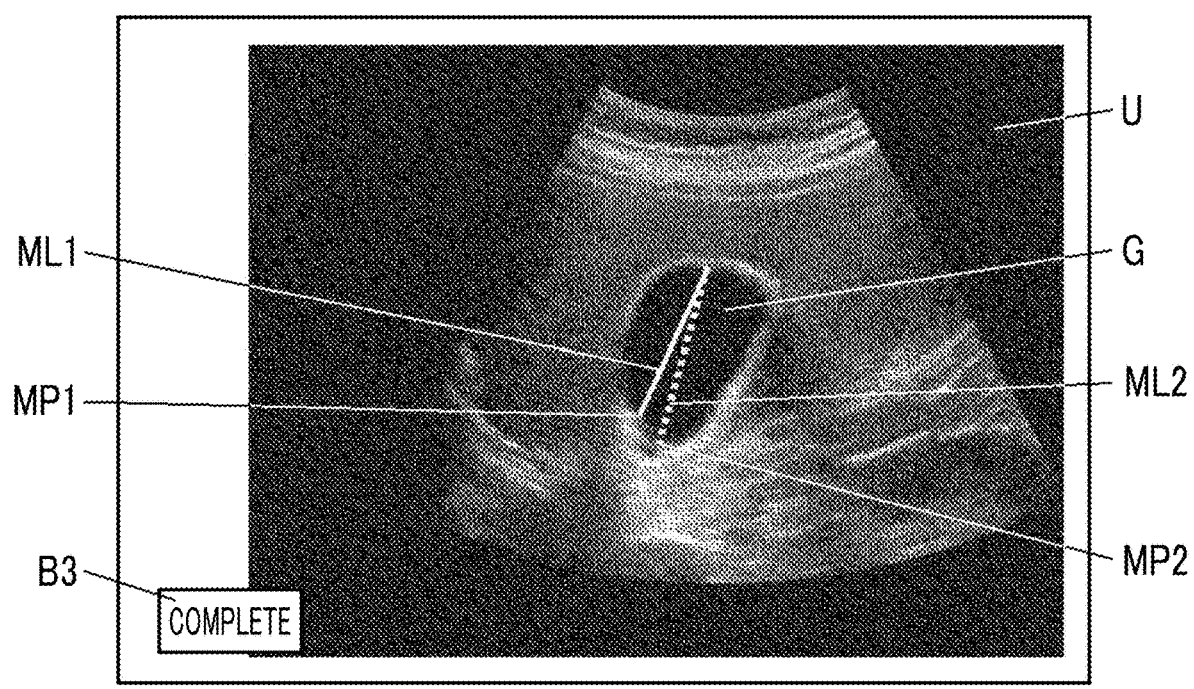
FIG. 21 is a diagram illustrating a modified measurement line.

In step S14, the measurement point modification acceptance unit 25 accepts a modification of the measurement point by the user through the operation unit 16. For example, as illustrated in FIG. 21, in a state where the position of a measurement point MP1 as the end point of the measurement line ML1 is moved to the position of a measurement point MP2 by the user through the operation unit 16 and a measurement line ML2 is displayed on the display unit 7, in a case where the completion button B3 is pressed by the user through the operation unit 16, the measurement point modification acceptance unit 25 determines that the modification of the measurement point is completed to accept the modification.

In step S15, the scan range modification unit 10 back-calculates a temporary detection region on the basis of the measurement point modified in step S14. For example, as illustrated in FIG. 22, the scan range modification unit 10 calculates a temporary detection region TR including the measurement line ML2 having the modified measurement point MP2 as the end point and a region representing the gallbladder G as the measurement target on the basis of the detection and measurement algorithm.

Figure 22:
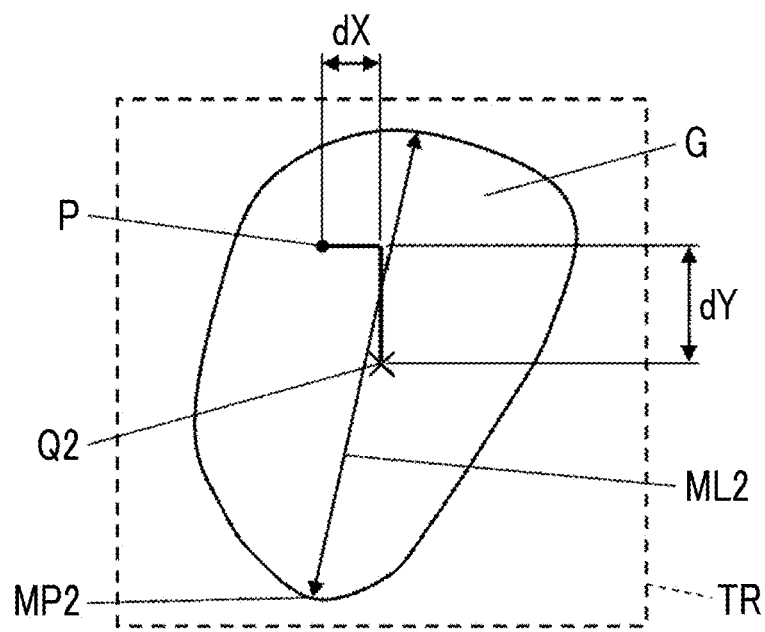
FIG. 22 is a schematic diagram illustrating a deviation amount of a scan range in Embodiment 3 of the invention.

In subsequent step S6, as illustrated in FIG. 22, the scan range modification unit 10 calculates deviation amounts dX and dY of the scan range SR1 on the basis of the measurement position P designated by the user in step S3 and a center Q2 of the temporary detection region TR calculated in step S15, and calculates the modification amount of the scan range SR1 from the deviation amounts dX and dY. The scan range modification unit 10 modifies the scan range SR1 using the modification amount.

In subsequent step S7, the scan range modification unit 10 stores a new scan range obtained in step S6 in the scan range memory 11 for each piece of user identification information set in step S1.

In step S8, in a case where there is no end instruction for the measurement operation of the ultrasound diagnostic apparatus 1A, the processing returns to step S2, and the processing of step S2 to step S5, step S13 to step S15, and step S6 to step S8 is performed again.

In a case where there is an end instruction for the measurement operation of the ultrasound diagnostic apparatus 1A in step S8, the operation of the ultrasound diagnostic apparatus 1A is ended.

As described above, with the ultrasound diagnostic apparatus 1A of Embodiment 3, since the temporary detection region TR is calculated on the basis of the measurement point modified by the user through the operation unit 16 and the scan range SR1 is modified on the basis of the position of the center Q2 of the temporary detection region TR and the measurement position P designated by the user, even in a case where there is a modification of the measurement point by the manual operation of the user through the operation unit 16, it is possible to modify the scan range by accurately reflecting the tendency of the measurement position designated by the user.

Figure 12:
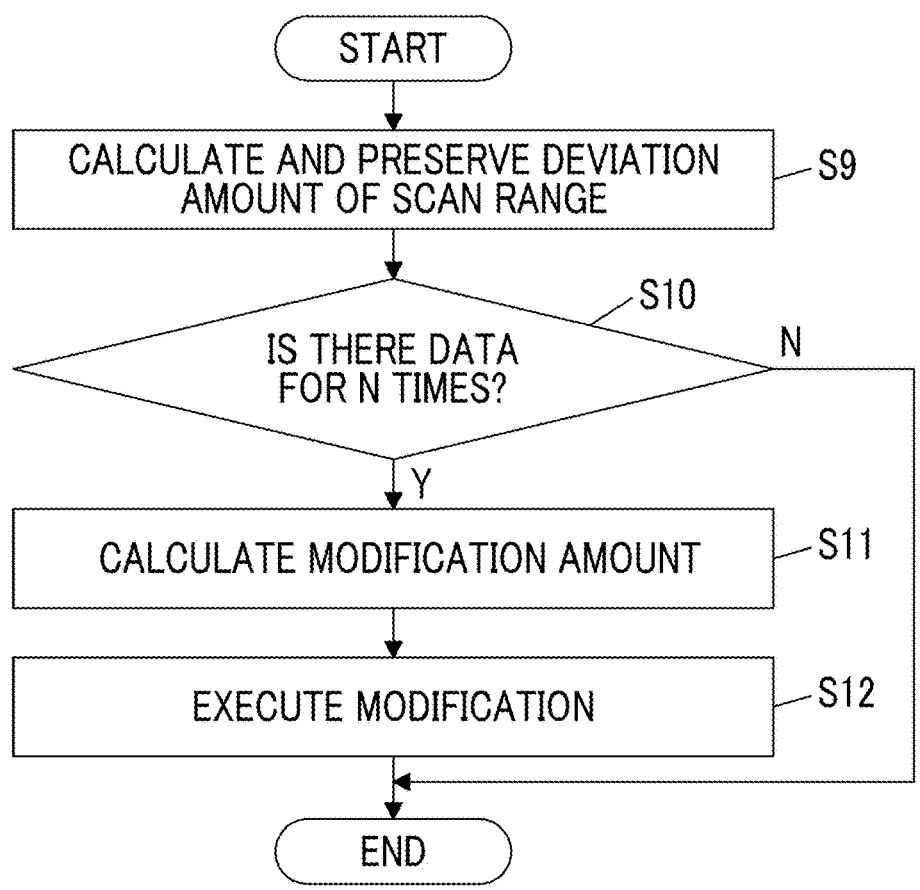
FIG. 12 is a flowchart illustrating a modification operation of a scan range in Embodiment 2 of the invention.

In Embodiment 3, the scan range is modified each time the measurement of the measurement target is performed, but as in the modification operation illustrated in the flowchart of FIG. 12, the scan range may be modified each time the measurement is performed N times.

In a case where the center Q2 of the temporary detection region TR calculated in step S15 is positioned outside the scan range SR1, it is possible to display the fact that the measurement point MP2 accepted by the measurement point modification acceptance unit 25 is greatly deviated from the measurement target on the display unit 7. As a result, the user can be alerted on the basis of the position on the ultrasound image designated as the measurement position P, and it is possible to prevent that the scan range is modified to a region not intended by the user.

Figure 23:
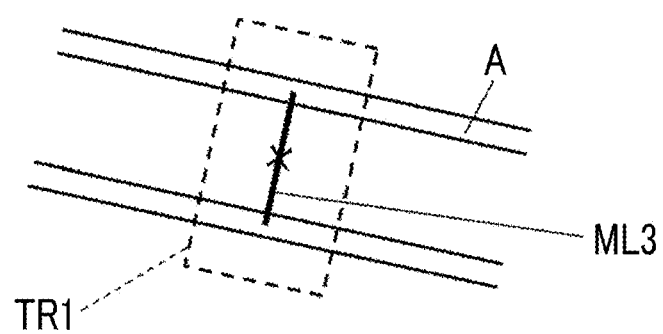
FIG. 23 is a diagram illustrating an example of a scan range set for a measurement target with a tubular structure.

In step S15, the scan range modification unit 10 calculates the temporary detection region TR including the measurement line ML2 and the region representing the gallbladder G, but it is possible to change the shape and size of the temporary detection region TR according to the measurement target. For example, as illustrated in FIG. 23, in case of measuring the diameter of a site A having a tubular structure such as the common bile duct and the inferior vena cava, since a measurement line ML3 extending along a direction perpendicular to a traveling direction of the site A is disposed on the ultrasound image, the scan range modification unit 10 can set the temporary detection region TR1 having a rectangular shape extending longer in a direction along the measurement line ML3 than the traveling direction of the site A.

Embodiment 4

Figure 24:
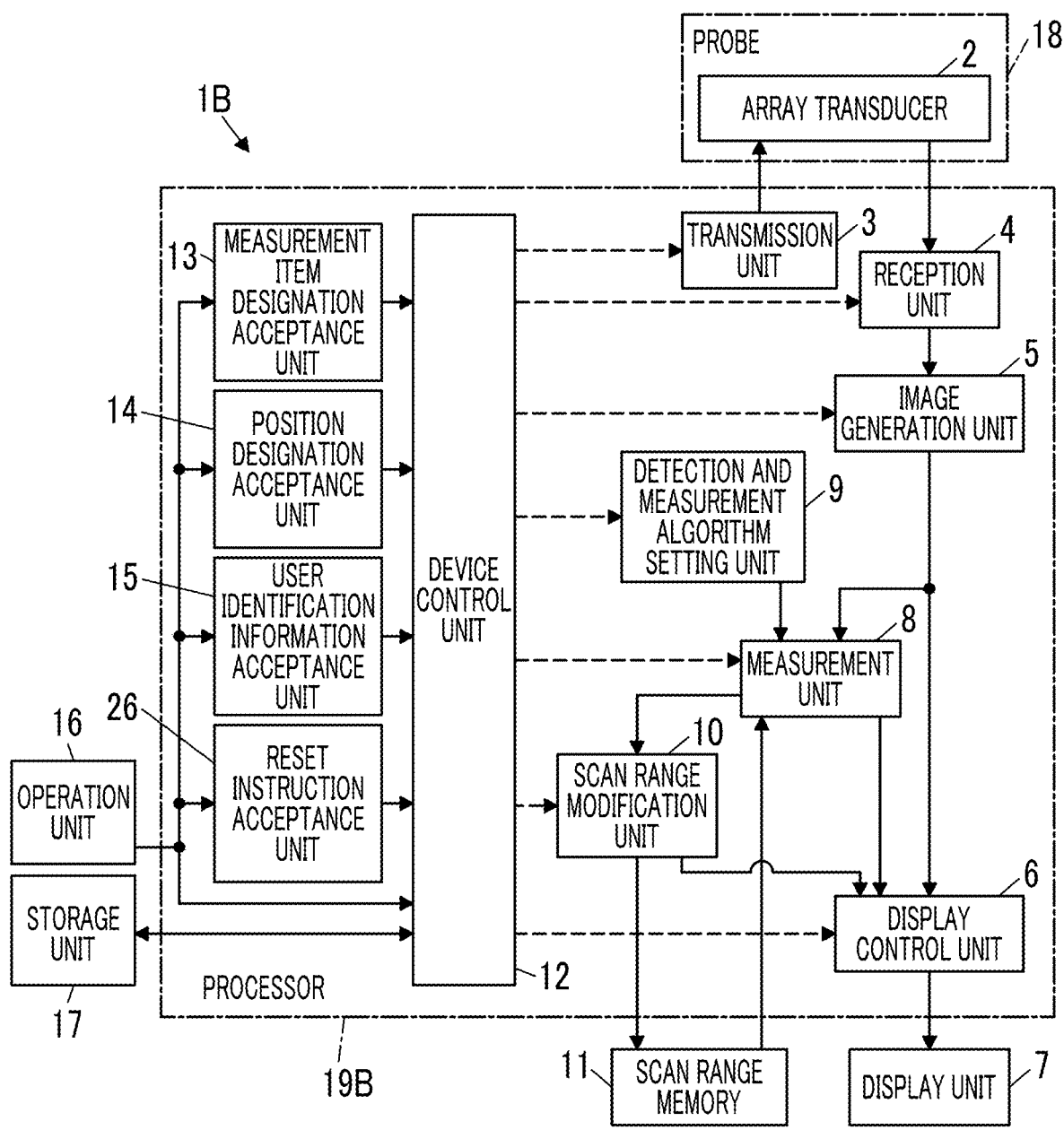
FIG. 24 is a block diagram illustrating a configuration of an ultrasound diagnostic apparatus according to Embodiment 4 of the invention.

In Embodiment 1 to Embodiment 3, the measurement unit 8 modifies the scan range for detecting the measurement target, but the modified scan range can be reset to the state before being modified. FIG. 24 illustrates a configuration of an ultrasound diagnostic apparatus 1B according to Embodiment 4. The ultrasound diagnostic apparatus 1B is obtained by further providing a reset instruction acceptance unit 26 to the ultrasound diagnostic apparatus 1 of Embodiment 1 illustrated in FIG. 1. As in the measurement item designation acceptance unit 13, the position designation acceptance unit 14, and the user identification information acceptance unit 15, the reset instruction acceptance unit 26 is connected to the device control unit 12 and the operation unit 16.

In addition, the transmission unit 3, the reception unit 4, the image generation unit 5, the display control unit 6, the measurement unit 8, the detection and measurement algorithm setting unit 9, the scan range modification unit 10, the device control unit 12, the measurement item designation acceptance unit 13, the position designation acceptance unit 14, the user identification information acceptance unit 15, and the reset instruction acceptance unit 26 constitute a processor 19B.

Figure 25:
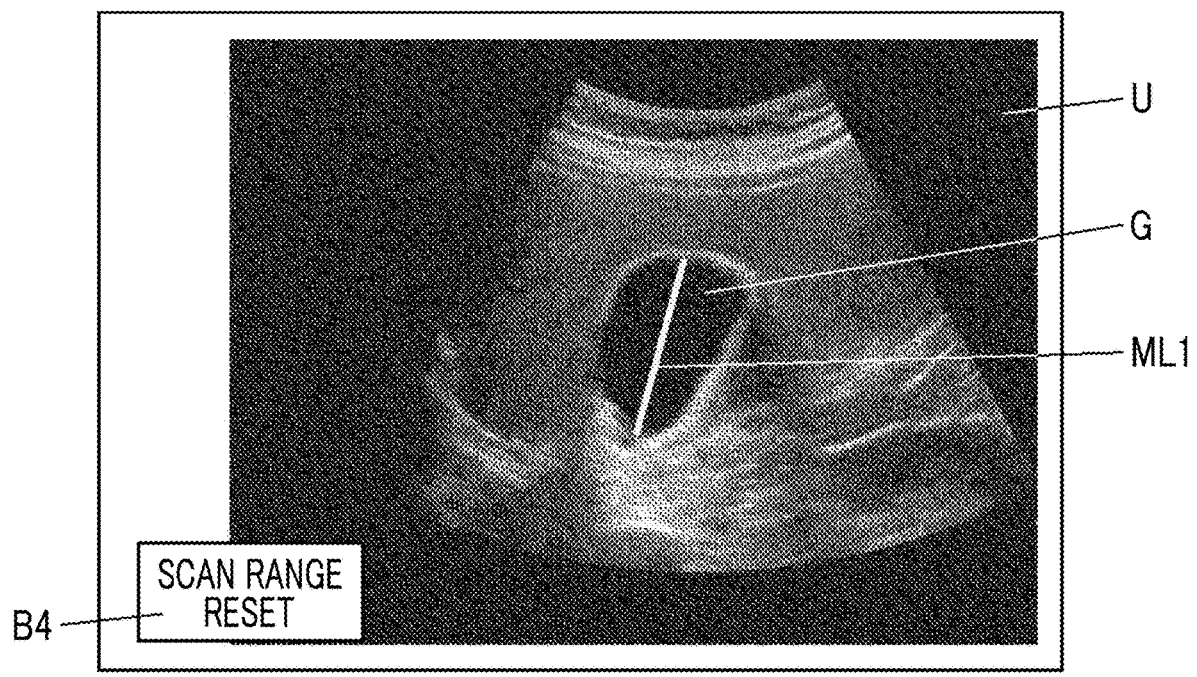
FIG. 25 is a diagram illustrating an example of a reset button for a scan range.

The reset instruction acceptance unit 26 of the processor 19B accepts an instruction to reset the scan range modified by the scan range modification unit 10 to the predetermined scan range SR1. Here, the instruction to reset the scan range is made by the user through the operation unit 16. For example, as illustrated in FIG. 25, a reset button B4 for resetting the scan range is displayed on the display unit 7 together with the ultrasound image U and the measurement result such as the measurement line ML1, and the scan range modified by the scan range modification unit 10 can be reset in a case where the reset button B4 is pressed by the user through the operation unit 16.

With the ultrasound diagnostic apparatus 1B of Embodiment 4, since the scan range modified by the scan range modification unit 10 can be reset to the predetermined scan range SR1, for example, in a case where the scan range is modified to a range not intended by the user or the like, it is possible to modify again the scan range by accurately reflecting the tendency of the measurement position designated by the user.

Embodiment 5

Figure 26:
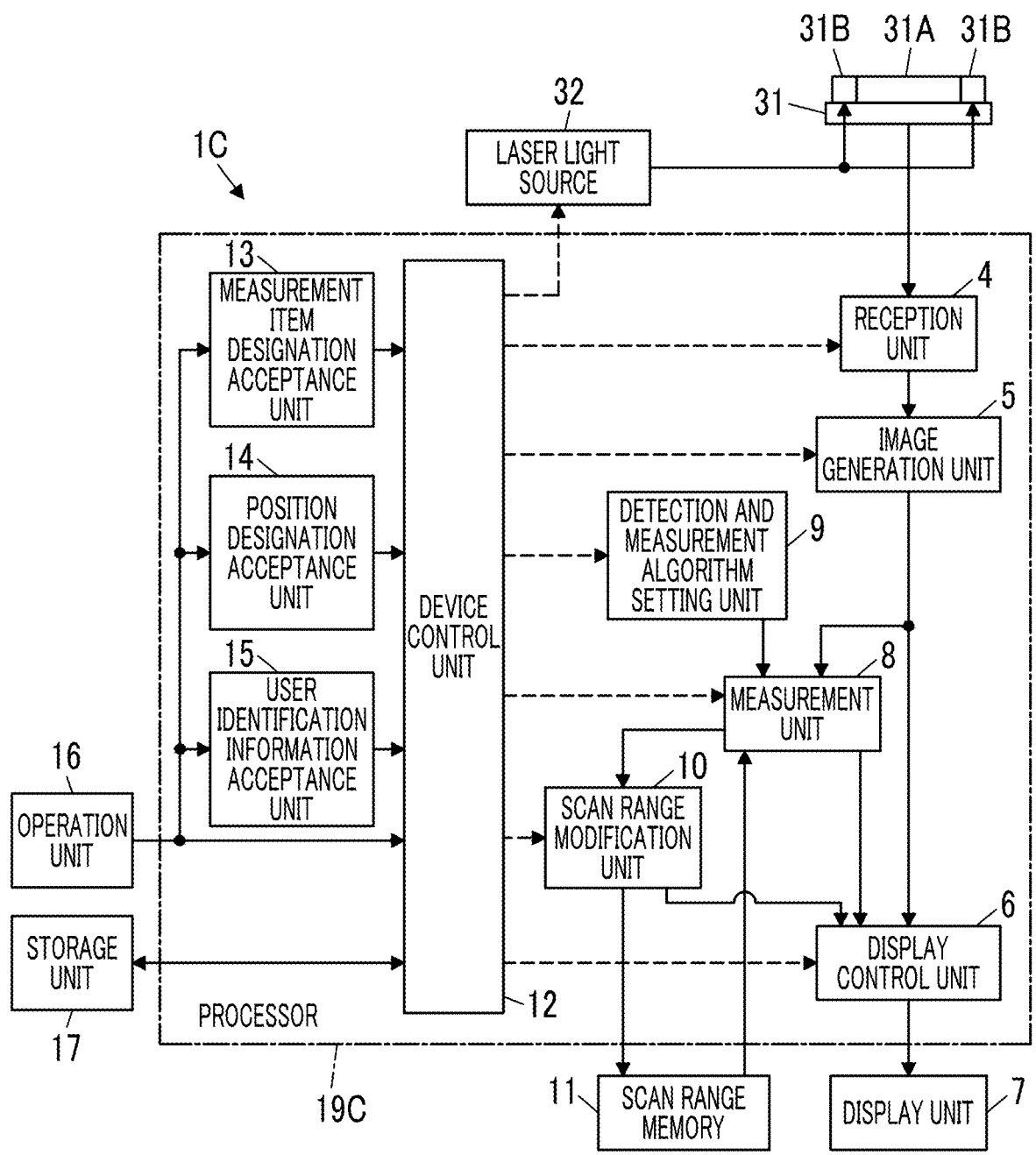
FIG. 26 is a block diagram illustrating a configuration of a photoacoustic wave diagnostic apparatus according to Embodiment 5 of the invention.

In Embodiment 1 to Embodiment 4, the ultrasound diagnostic apparatus is described, but the invention can be applied to an acoustic wave diagnostic apparatus other than the ultrasound diagnostic apparatus, such as a photoacoustic wave diagnostic apparatus. FIG. 26 illustrates a configuration of a photoacoustic wave diagnostic apparatus 1C according to Embodiment 5. The photoacoustic wave diagnostic apparatus 1C is obtained such that the ultrasound diagnostic apparatus 1 of Embodiment 1 illustrated in FIG. 1 comprises a probe 31 instead of the probe 18 and comprises a laser light source 32 instead of the transmission unit 3.

The probe 31 has an array transducer 31A similar to the array transducer 2 of the ultrasound diagnostic apparatus 1 illustrated in FIG. 1 and a pair of laser light irradiation units 31B disposed on both end portions of the array transducer 31A. The array transducer 31A is connected to the reception unit 4. In addition, the pair of laser light irradiation units 31B is connected to the laser light source 32, and the laser light source 32 is connected to the device control unit 12.

Further, the reception unit 4, the image generation unit 5, the display control unit 6, the measurement unit 8, the detection and measurement algorithm setting unit 9, the scan range modification unit 10, the device control unit 12, the measurement item designation acceptance unit 13, the position designation acceptance unit 14, and the user identification information acceptance unit 15 constitute a processor 19C.

Figure 27:
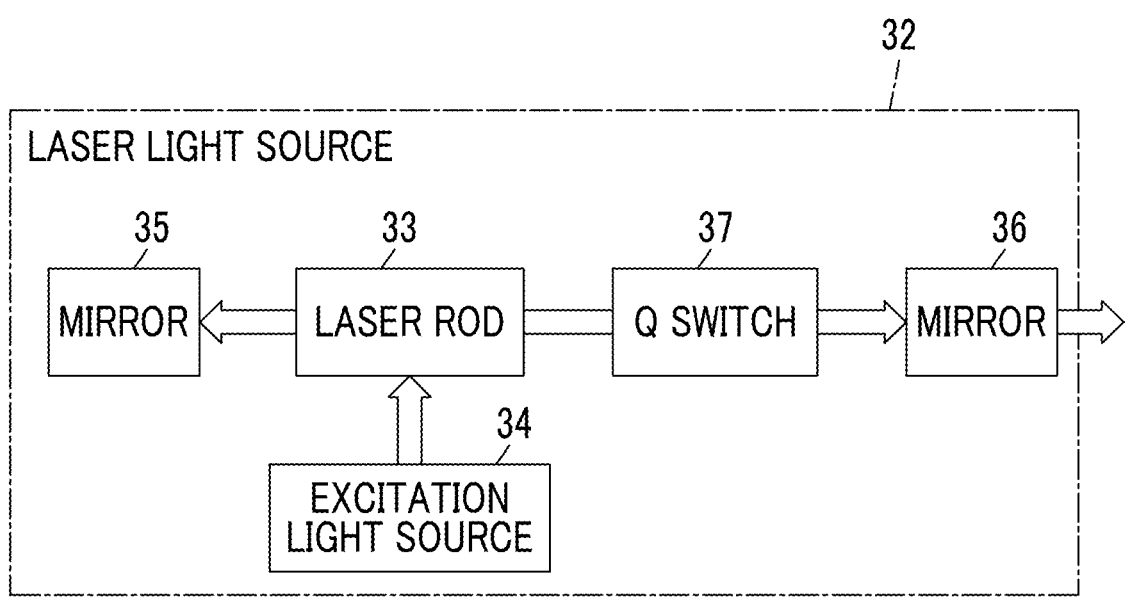
FIG. 27 is a block diagram illustrating an internal configuration of a laser light source in Embodiment 5 of the invention.

The laser light source 32 of the photoacoustic wave diagnostic apparatus 1C emits pulsed laser light under the control of the device control unit 12. As illustrated in FIG. 27, the laser light source 32 has a laser rod 33, an excitation light source 34, a mirror 35, a mirror 36, and a Q switch 37. The laser rod 33 is a laser medium, and for example, an alexandrite crystal, an Nd:YAG crystal, or the like can be used for the laser rod 33. The excitation light source 34 is a light source irradiating the laser rod 33 with excitation light, and for example, a light source such as a flash lamp and a laser diode can be used for the excitation light source 34.

The mirrors 35 and 36 face each other with the laser rod 33 interposed therebetween, the mirrors 35 and 36 constitute an optical resonator. In the optical resonator, the mirror 36 is the output side. In the optical resonator, the Q switch 37 is inserted, and a state in which the insertion loss in the optical resonator is large is rapidly changed to a state in which the insertion loss is small by the Q switch 37, thereby obtaining pulsed laser light. The pulsed laser light emitted from the mirror 36 on the output side of the laser light source 32 is guided to the laser light irradiation units 31B of the probe 31 through a light guide member (not illustrated) or the like.

The laser light irradiation units 31B of the probe 31 are disposed on the both ends of the array transducer 31A, and comes into contact with the body surface of the subject to emit the pulsed laser light, which is guided from the laser light source 32 through the light guide member (not illustrated) or the like, to the inside of the subject. The pulsed laser light emitted to the inside of the subject in this manner is absorbed as heat energy by an in-vivo substance such as hemoglobin contained in the subject, and the in-vivo substance that has absorbed the pulsed laser light expands and contracts to generate a photoacoustic wave.

The array transducer 31A of the probe 31 has the same configuration as the array transducer 2 illustrated in FIG. 1, but the array transducer 31A receives photoacoustic wave generated by the emission of the pulsed laser light from the laser light source 32 through the laser light irradiation units 31B to the inside of the subject, and outputs a photoacoustic wave reception signal to the reception unit 4. As in the reception signal based on the ultrasound echo in Embodiment 1, the photoacoustic wave reception signal obtained in this manner is sent to the image generation unit 5, and a photoacoustic image is generated by the image generation unit 5. The photoacoustic image generated in this manner is displayed on the display unit 7 through the display control unit 6, and is sent to the measurement unit 8 to be used in the measurement of the measurement target.

The measurement unit 8 detects the measurement target by setting a scan range on the photoacoustic image generated by the image generation unit 5 and measures the detected measurement target on the basis of the detection and measurement algorithm set by the detection and measurement algorithm setting unit 9.

The scan range modification unit 10 modifies the scan range SR1 set on the photoacoustic image by the measurement unit 8, and stores a newly obtained scan range in the scan range memory 11. As a result, from the next measurement, the measurement unit 8 sets the new scan range stored in the scan range memory 11 on the photoacoustic image, and detects the measurement target.

As described above, the invention is also applied to the acoustic wave diagnostic apparatus such as the photoacoustic wave diagnostic apparatus 1C.

EXPLANATION OF REFERENCES 1, 1A, 1B: ultrasound diagnostic apparatus
1C: photoacoustic wave diagnostic apparatus
2, 31A: array transducer
3: transmission unit
4: reception unit
5: image generation unit
6: display control unit
7: display unit
8: measurement unit
9: detection and measurement algorithm setting unit
10: scan range modification unit
11: scan range memory
12: device control unit
13: measurement item designation acceptance unit
14: position designation acceptance unit
15: user identification information acceptance unit
16: operation unit
17: storage unit
18: probe
19: processor
20: amplification unit
21: AD conversion unit
22: signal processing unit
23: DSC
24: image processing unit
25: measurement point modification acceptance unit
26: reset instruction acceptance unit
31B: laser light irradiation unit
32: laser light source
33: laser rod
34: excitation light source
35, 36: mirror
37: Q switch
A: site
B1: OK button
B2: cancel button
B3: completion button
B4: reset button
DR: detection region
dX, dY: deviation amount F: finger
G: gallbladder
L1, L2: distance
M: list
ML1, ML2, ML3: measurement line
MP1, MP2: measurement point
P: measurement position
Q1, Q2: center
SR1, SR2, SR3, SR4, SR5, SR6: scan range
TR, TR1: temporary detection region
U: ultrasound image

What is claimed is:

1. An acoustic wave diagnostic apparatus comprising:
a display unit that displays an acquired acoustic wave image;
an operation unit that is used for a user to perform an input operation;
a processor that accepts user identification information through the operation unit, accepts designation of a measurement item relating to a measurement target through the operation unit, sets a detection and measurement algorithm on the basis of the measurement item, accepts designation of a position of the measurement target on the acoustic wave image displayed on the display unit through the operation unit, detects the measurement target by scanning a detection region in a scan range and measures the detected measurement target on the basis of the position of the measurement target and the detection and measurement algorithm to cause the display unit to display a measurement result including a measurement point, and modifies the scan range; and
a scan range memory that stores the scan range modified by the processor in association with the user identification information,
wherein, from next measurement by the user, the processor detects the measurement target using the scan range stored in the scan range memory.

2. The acoustic wave diagnostic apparatus according to claim 1,
wherein the processor modifies at least one of a size or a position of the scan range.

3. The acoustic wave diagnostic apparatus according to claim 1,
wherein the processor modifies the scan range on the basis of the position of the measurement target accepted and the position of the measurement target detected.

4. The acoustic wave diagnostic apparatus according to claim 2,
wherein the processor modifies the scan range on the basis of the position of the measurement target accepted and the position of the measurement target detected.

5. The acoustic wave diagnostic apparatus according to claim 3,
wherein the processor calculates reliability of detection of the measurement target in each detection region while scanning the detection region in the scan range, and modifies the scan range on the basis of the position of the measurement target accepted and a position of a center of the detection region having the maximum reliability calculated.

6. The acoustic wave diagnostic apparatus according to claim 4,
wherein the processor calculates reliability of detection of the measurement target in each detection region while scanning the detection region in the scan range, and modifies the scan range on the basis of the position of the measurement target accepted and a position of a center of the detection region having the maximum reliability calculated.

7. The acoustic wave diagnostic apparatus according to claim 3,
wherein the processor calculates a deviation amount between the position of the measurement target accepted and the position of the measurement target detected, and modifies the scan range on the basis of statistical data of the deviation amounts after the user performs a predetermined number of times of measurement.

8. The acoustic wave diagnostic apparatus according to claim 4,
wherein the processor calculates a deviation amount between the position of the measurement target accepted and the position of the measurement target detected, and modifies the scan range on the basis of statistical data of the deviation amounts after the user performs a predetermined number of times of measurement.

9. The acoustic wave diagnostic apparatus according to claim 5,
wherein the processor calculates a deviation amount between the position of the measurement target accepted and the position of the measurement target detected, and modifies the scan range on the basis of statistical data of the deviation amounts after the user performs a predetermined number of times of measurement.

10. The acoustic wave diagnostic apparatus according to claim 1, further comprising:
wherein the processor accepts a modification of a position of the measurement point through the operation unit, and modifies the scan range on the basis of the position of the measurement target accepted and the position of the measurement point accepted.

11. The acoustic wave diagnostic apparatus according to claim 2, further comprising:
wherein the processor accepts a modification of a position of the measurement point through the operation unit, and modifies the scan range on the basis of the position of the measurement target accepted and the position of the measurement point accepted.

12. The acoustic wave diagnostic apparatus according to claim 10,
wherein the processor calculates a temporary detection region for detecting the measurement target on the basis of the position of the measurement point accepted, and modifies the scan range on the basis of the position of the measurement target and a position of a center of the temporary detection region.

13. The acoustic wave diagnostic apparatus according to claim 11,
wherein the processor calculates a temporary detection region for detecting the measurement target on the basis of the position of the measurement point accepted, and modifies the scan range on the basis of the position of the measurement target and a position of a center of the temporary detection region.

14. The acoustic wave diagnostic apparatus according to claim 12,
wherein the processor causes the display unit to display that the position of the measurement point accepted is deviated, in a case where the position of the center of the temporary detection region is positioned outside the scan range.

15. The acoustic wave diagnostic apparatus according to claim 13,
wherein the processor causes the display unit to display that the position of the measurement point accepted is deviated, in a case where the position of the center of the temporary detection region is positioned outside the scan range.

16. The acoustic wave diagnostic apparatus according to claim 1,
wherein the processor causes the display unit to display that the scan range is modified.

17. The acoustic wave diagnostic apparatus according to claim 1,
wherein the processor accepts a reset instruction to return the scan range modified to an initial scan range through the operation unit, and detects the measurement target using the initial scan range in a case where the reset instruction is accepted.

18. The acoustic wave diagnostic apparatus according to claim 1,
wherein the processor causes the display unit to display the scan range in a case where the designation of the position of the measurement target is accepted.

19. The acoustic wave diagnostic apparatus according to claim 1,
wherein the acoustic wave image is an ultrasound image or a photoacoustic image.

20. A control method of an acoustic wave diagnostic apparatus, the control method comprising:
displaying an acquired acoustic wave image;
accepting user identification information from a user;
accepting designation of a measurement item relating to a measurement target from the user;
setting a detection and measurement algorithm on the basis of the accepted measurement item;
accepting designation of a position of the measurement target on the acoustic wave image from the user;
detecting the measurement target by scanning a detection region in a scan range and measuring the detected measurement target on the basis of the accepted position of the measurement target and the detection and measurement algorithm to display a measurement result including a measurement point;
modifying the scan range; and
storing the modified scan range in association with the user identification information,
wherein, from next measurement by the user, the measurement target is detected using the stored scan range.

* * * * *